United States Patent [19]

Taguchi et al.

[11] Patent Number: 4,853,469

[45] Date of Patent: Aug. 1, 1989

[54] QUINOLINECARBOXYLIC ACID DERIVATIVE STARTING COMPOUNDS

[75] Inventors: Masahiro Taguchi, Hirakata; Hirosato Kondo, Suita; Yoshimasa Inoue, Osaka; Yoshihiro Kawahata, Minoo; Goro Tsukamoto, Toyonaka, all of Japan

[73] Assignee: Kanebo, Ltd., Japan

[21] Appl. No.: 225,369

[22] Filed: Jul. 28, 1988

Related U.S. Application Data

[62] Division of Ser. No. 178,603, Apr. 7, 1988, Pat. No. 4,808,584.

[30] Foreign Application Priority Data

Apr. 7, 1987 [JP] Japan .................................. 62-85319
Oct. 19, 1987 [JP] Japan ................................ 62-264681

[51] Int. Cl.$^4$ .................... A61K 31/535; A61K 31/47
[52] U.S. Cl. ........................................... 544/99; 546/80
[58] Field of Search ............................. 544/99; 546/80

[56] References Cited

U.S. PATENT DOCUMENTS

| | | | |
|---|---|---|---|
| 4,382,892 | 5/1983 | Hayakawa et al. | 540/575 |
| 4,426,381 | 1/1984 | Matsumura et al. | 514/254 |
| 4,659,734 | 4/1987 | Enomoto et al. | 514/255 |
| 4,687,770 | 8/1987 | Chu | 544/99 X |
| 4,689,325 | 8/1987 | Chu | 544/99 X |

FOREIGN PATENT DOCUMENTS 058392 8/1982 European Pat. Off. .
193283 9/1986 European Pat. Off. .

Primary Examiner—Richard L. Raymond
Attorney, Agent, or Firm—Wegner & Bretschneider

[57] ABSTRACT

Novel quinolinecarboxylic derivatives of the formula:

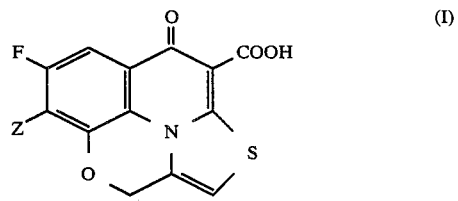

wherein Z is

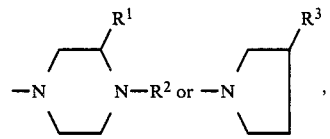

in which $R^1$ is hydrogen atom or a lower alkyl, $R^2$ is hydrogen atom, hydroxyl or a lower alkyl and $R^3$ is hydrogen atom, hydroxyl or an amino, and a pharmaceutical salt thereof have excellent antibacterial activities and are useful as an antibacterial agent.

2 Claims, No Drawings

QUINOLINECARBOXYLIC ACID DERIVATIVE STARTING COMPOUNDS

This is a division of application Ser. No. 178,603, filed 4/7/88, now U.S. Pat. No. 4,808,584.

The present invention relates to novel quinolinecarboxylic acid derivatives and an antibacterial agent containing said compound as an active ingredient. More particularly, the present invention relates to novel quinolinecarboxylic derivatives represented by the following formula (I):

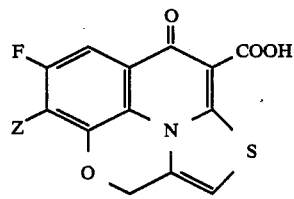

wherein Z is

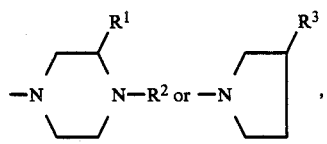

in which $R^1$ is hydrogen atom or a lower alkyl, $R^2$ is hydrogen atom, hydroxyl or a lower alkyl and $R^3$ is a hydrogen atom, hydroxyl or an amino group, and a pharmaceutically acceptable salt thereof, and an antibacterial agent containing said compound as an active ingredient.

PRIOR ART

Since the finding of nalidixic acid as a synthetic antibacterial agent, various quinolinecarboxylic acid derivatives have hitherto been examined for the purpose of improvement of an antibacterial activity. Among them, ofloxacin having a condensed tricyclic structure of the following formula has been reported to show an excellent antibacterial activity and has now clinically been used (U.S. Pat. No. 4,382,892).

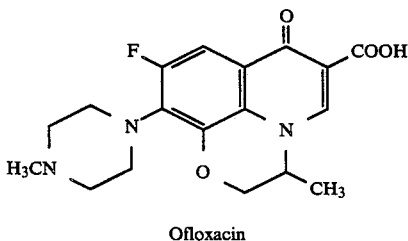

Ofloxacin

BRIEF SUMMARY OF THE INVENTION

The present inventors have worked on finding novel quinolinecarboxylic acid derivatives having improved anti-bacterial activities.

An object of the present invention is to provide a novel quinolinecarboxylic acid derivatives having improved antibacterial activities and an excellent antibacterial agent containing the same as an active ingredient.

DETAILED DESCRIPTION OF THE INVENTION

The present inventors have found that the quinolinecarboxylic acid derivative of the following formula (I) and a pharmaceutically acceptable salt thereof showed potent antibacterial activities with a wider antibacterial spectrum.

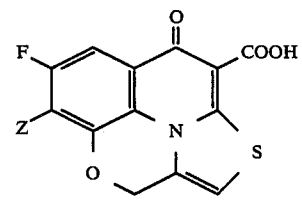

wherein Z is a cyclic amino group such as

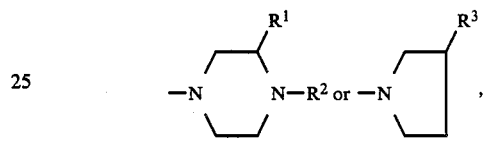

in which $R^1$ is hydrogen atom or a lower alkyl, $R^2$ is hydrogen atom, hydroxyl or a lower alkyl and $R^3$ is hydrogen atom, hydroxyl or an amino group.

Through the present specification and claims, the term "lower alkyl" denotes a straight chain or branched chain alkyl having 1 to 4 carbon atoms, such as methyl, ethyl, n-propyl, isopropyl, n-butyl, sec-butyl, tert-butyl, and the like.

Suitable examples of the above cyclic amino group are 1-piperazinyl, 4-methyl-1-piperazinyl, 4-ethyl-1-piperazinyl, 3-methyl-1-piperazinyl, 4-hydroxy-1-piperazinyl, 1-pyrrolidinyl, 3-hydroxy-1-pyrrolidinyl, 3-amino-1-pyrrolidinyl, and the like.

The compounds of the present invention include a pharmaceutically acceptable salt of the compound of the formula (I). Preferred pharmaceutically acceptable salt of the compound (I) of the present invention are metallic salts such as a sodium salt, potassium salt and calcium salt, an ammonium salt and basic amino acid salts such as salts with lysine and arginine at the carboxyl; and where Z is

in which $R^1$ and $R^2$ are as defined above, or 3-amino-1-pyrrolidinyl, addition salts of inorganic acids such as hydrochloric acid and sulfuric acid, and of organic acids such as maleic acid, fumaric acid, tartaric acid and methanesulfonic acid are also included.

The compounds of the present invention can be prepared by, for example, the following process (A) or (B).

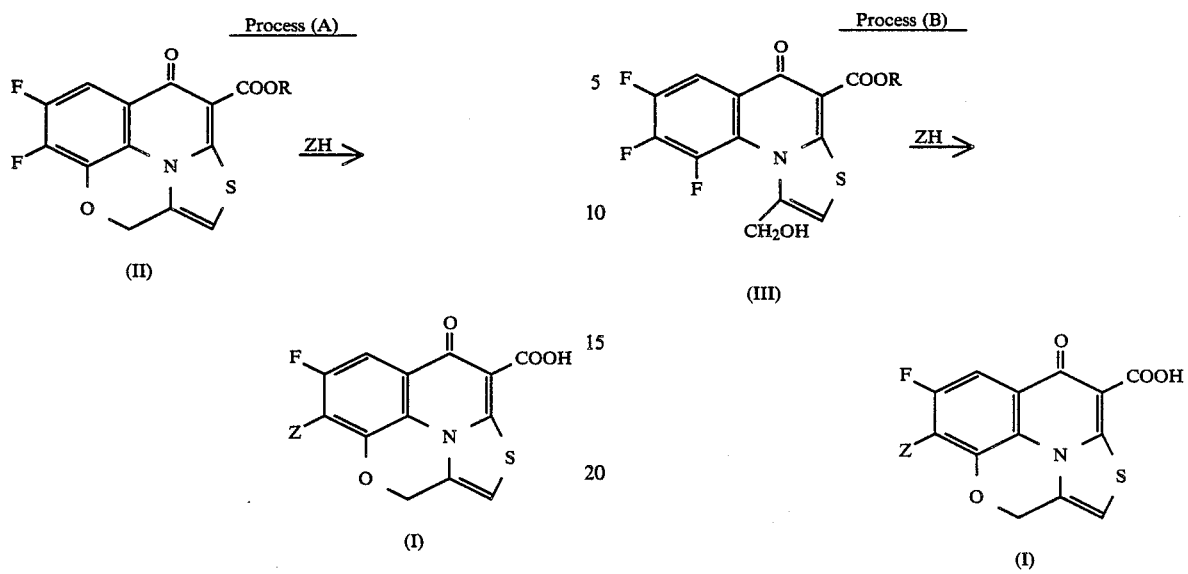

Process (A) / Process (B)

wherein R is hydrogen atom or a lower alkyl and Z is as defined above.

The compound (I) of the present invention can be prepared by reacting a compound (II) with a cyclic amine (ZH) or an acid addition salt thereof in a polar organic solvent such as dimethylsulfoxide or N,N-dimethylformamide in the presence of an acid capturing agent, and if necessary, hydrolyzing the obtained product. When the compound (II) in which R is hydrogen atom is reacted with the cyclic amine (ZH) or acid addition salt thereof, the compound (I) of the present invention is directly prepared. When the compound (II) in which R is a lower alkyl is reacted with the cyclic amine (ZH) or acid addition salt thereof, a lower alkyl ester of the compound (I) of the present invention is prepared, which is then hydrolyzed in the conventional manner to give the compound (I) of the present invention.

The acid capturing agent includes a tertiary amine such as triethylamine or an inorganic base such as sodium carbonate or potassium carbonate. An excess amount of the above cyclic amine can also be employed as the acid capturing agent. In the case that the tertiary amine or the inorganic base is employed as the acid capturing agent, the reaction is usually carried out in such a way that one mole of the compound (II) is reacted with 1 to 1.5 moles of the cyclic amine or the acid addition salt thereof employing 2 to 6 moles of the acid capturing agent. When the acid capturing agent is the excess cyclic amine (ZH), one mole of the compound (II) is usually reacted with 3 to 7 moles of the cyclic amine (ZH).

The reaction temperature ranges from 30° to 150° C., preferably from 50° to 120° C. The reaction is usually carried out for about 30 minutes to about 50 hours though it may vary depending on the kind of the cyclic amine and the reaction temperature.

wherein Z and R are as defined above.

The compound (I) of the present invention can be prepared by reacting a compound (III) with the cyclic amine (ZH) or an acid addition salt thereof in a polar organic solvent such as dimethylsulfoxide or N,N-dimethylformamide in the presence of an acid capturing agent, and if necessary, hydrolyzing the obtained product. When the compound (III) in which R is hydrogen atom is reacted with the cyclic amine (ZH) or acid addition salt thereof, the compound (I) of the present invention is directly prepared. When the compound (III) in which R is a lower alkyl is reacted with the cyclic amine (ZH) or acid addition salt thereof, a lower alkyl ester of the compound (I) of the present invention is prepared, which is then hydrolyzed in the conventional manner to give the compound (I) of the present invention.

The acid capturing agent includes a tertiary amine such as triethylamine or an inorganic base such as sodium carbonate or potassium carbonate. An excess amount of the above cyclic amine can also be employed as the acid capturing agent. In the case that the tertiary amine or the inorganic base is employed as the acid capturing agent, the reaction is usually carried out in such a way that one mole of the compound (III) is reacted with 1 to 1.5 moles of the cyclic amine or the acid addition salt thereof employing 3 to 10 moles of the acid capturing agent. When the acid capturing agent is the excess cyclic amine (ZH), one mole of the compound (III) is usually reacted with 4 to 8 moles of the cyclic amine (ZH).

The reaction temperature ranges from 30° to 150° C., preferably from 50° to 120° C. The reaction is usually carried out for about 30 minutes to about 50 hours though it may vary depending on the kind of the cyclic amine and the reaction temperature.

Further among the compounds (I) of the present invention, a compound of the formula (I) in which Z is 3-amino-1-pyrrolidinyl can be prepared by the following process (C).

Process (C)

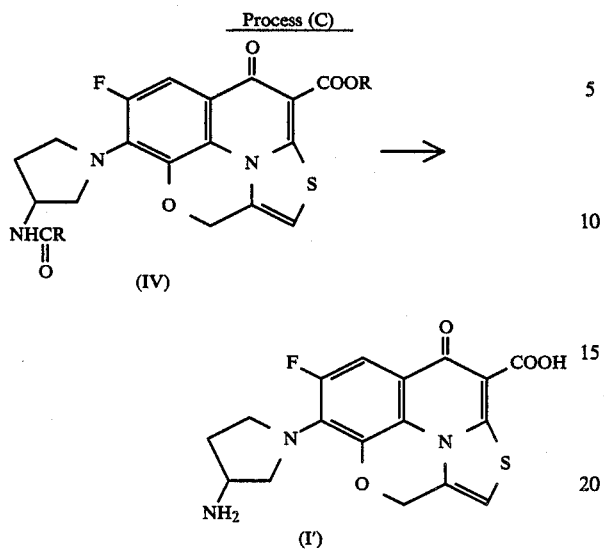

wherein R is as defined above.

That is, a compound (IV), prepared from the compound (II) or (III) and 3-acylaminopyrrolidine in accordance with the above process (A) or (B), is hydrolyzed to prepare a compound (I') of the present invention (i.e. Z in the formula (I) is 3-amino-1-pyrrolidinyl). The hydrolysis can be conducted in the conventional manner preferably with alkali.

The compound (I) of the present invention thus prepared by the above process (A), (B) or (C) can be isolated and purified by the conventional procedure, for example, silica-gel column chromatography or recrystallization. The compound (I) of the present invention can also be converted into pharmaceutically acceptable salts thereof by the conventional procedure.

The starting compound (II) in the above process (A) is a novel compound and prepared by the following process (a), (b) or (c). The starting compound (III) in the above process (B) is obtained in the following process (b) as an intermediate compound.

Process (a)

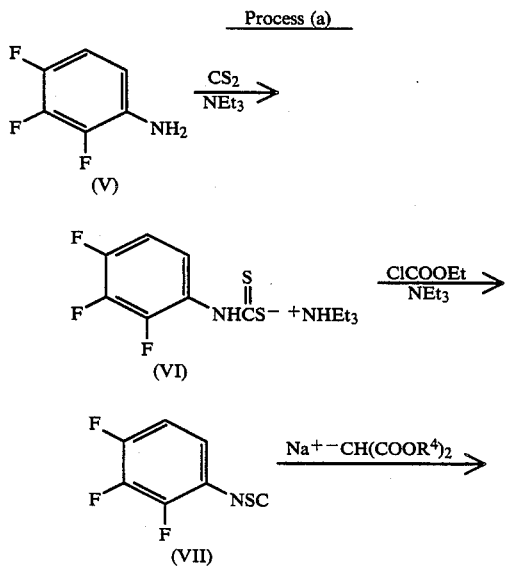

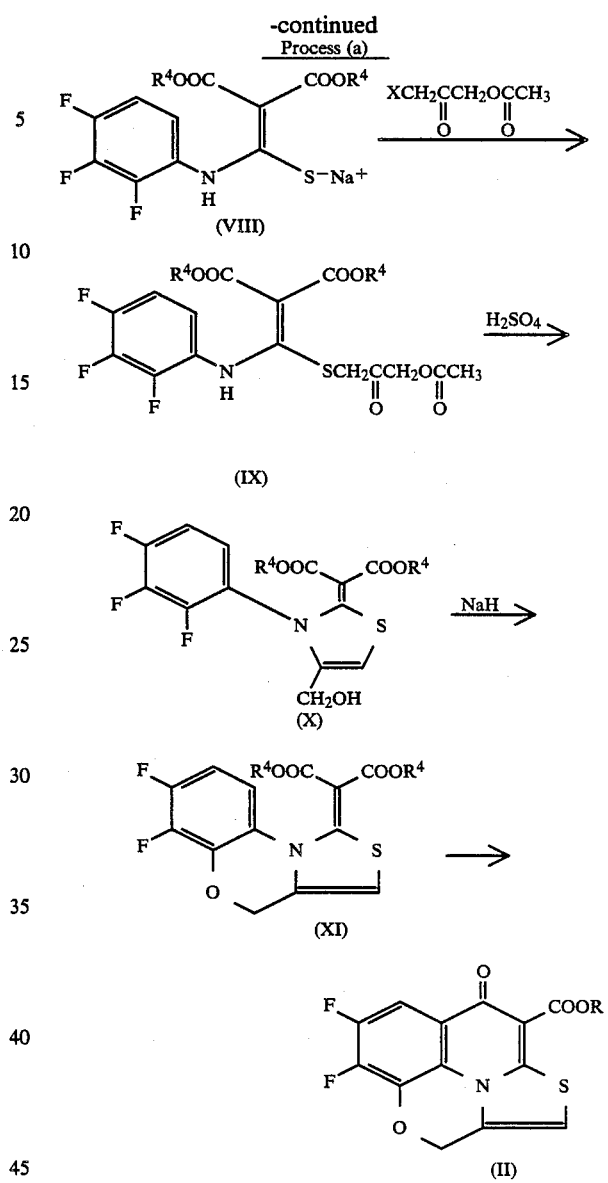

wherein R is as defined above, $R^4$ is a lower alkyl and X is a halogen atom.

That is, first 2,3,4-trifluoroaniline (V) is reacted with carbon disulfide in the presence of triethylamine to produce triethylammonium N-(2,3,4-trifluorophenyl)dithiocarbamate (VI). Then the compound (VI) is reacted with ethyl chloroformate in an organic solvent such as chloroform or methylene chloride in the presence of triethylamine to give 2,3,4-trifluorophenylisothiocayanate (VII). The compound (VII) is then reacted with di(lower alkyl) malonate sodium salt, which is prepared from di(lower alkyl) malonate and sodium hydride, in an organic solvent such as tetrahydrofuran or dioxane to give di(lower alkyl) [(2,3,4-trifluoroanilino)(mercapto)methylene]malonate sodium salt (VIII). The compound (VIII) is then reacted with 1-acetoxy-3-halogenoacetone in an organic solvent such as N,N-dimethylformamide, dimethylsulfoxide or acetonitrile to give di(lower alkyl)[(2,3,4-trifluoroanilino)(3-acetoxy-2-oxopropylthio)methylene]malonate (IX). The compound (IX) is then reacted with sulfuric acid to give di(lower alkyl)[3-(2,3,4-trifluorophenyl)-4-hydroxymethyl-2- thiazolidene]malonate (X). The compound (X) is then reacted with sodium hydride in an organic solvent such as dioxane, tetrahydrofuran or N,N-dimethylformamide to give di(lower alkyl)(6,7-difluoro-1H,4H-thiazolo[4,3-c][1,4]benzoxazin-1-ylidene)malonate (XI).

Finally the compound (XI) is heated with a condensing agent such as polyphosphoric acid or polyphosphoric acid ethyl ester and this is, if necessary, followed by hydrolysis of the product to give the compound (II). That is, the compound (XI) is heated with the condensing agent to give the compound (II) in which R is a lower alkyl (ester form), which is then hydrolyzed to give the compound (II) in which R is hydrogen atom. The hydrolysis is preferably carried out with sulfuric acid. The above ester can also be hydrolyzed without isolation, i.e. after heating the compound (XI) with the condensing agent, the reaction mixture is further heated with addition of sulfuric acid to give the compound (II) in which R is hydrogen atom.

Process (b)

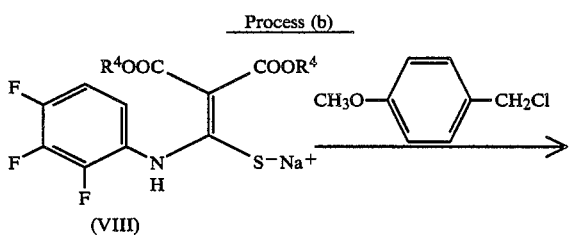

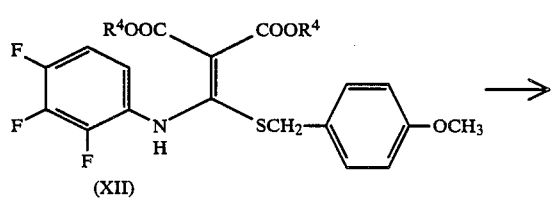

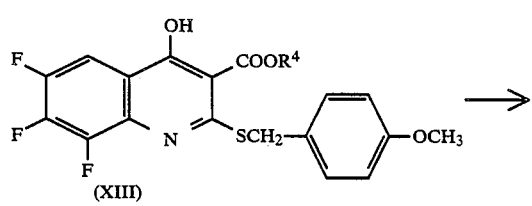

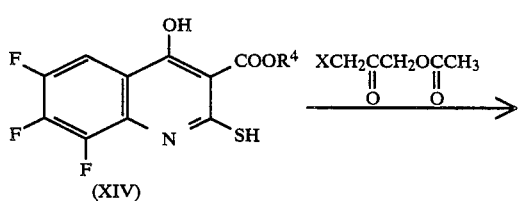

-continued
Process (b)

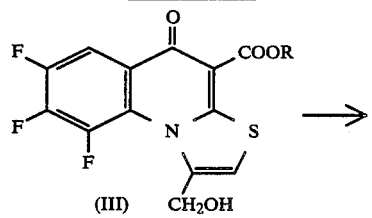

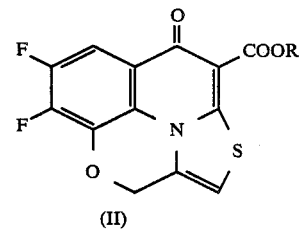

wherein R, R$^4$ and X are as defined above.

That is, the compound (VIII) prepared in the above process (a) is reacted with p-methoxybenzyl chloride in a polar organic solvent such as N,N-dimethylformamide to give di(lower alkyl)[(2,3,4-trifluoroanilino)(p-methoxybenzylthio)methylene]malonate (XII). The compound (XII) is then heated in a high boiling temperature solvent such as diphenyl ether to give lower alkyl 4-hydroxy-6,7,8-trifluoro-2-(p-methoxybenzylthio)-quinoline-3-carboxylate (XIII). The compound (XIII) is then treated with a mixture of trifluoromethanesulfonic acid and trifluroacetic acid to remove the p-methoxybenzyl group, yielding a lower alkyl 4-hydroxy-2-mercapto-6,7,8-trifluoroquinoline-3-carboxylate (XIV). The compound (XIV) is then reacted with 1-acetoxy-3-halogenoacetone in a solvent of a halogenated compound such as chloroform, methylene chloride in the presence of a tertiary amine such as triethylamine to give the lower alkyl 2-(3-acetoxy-2-oxopropylthio)-6,7,8-trifluoro-4-hydroxyquinoline-3-carboxylate (XV). The compound (XV) is then cyclized with conc. sulfuric acid and this is, if necessary, followed by hydrolysis of the product to give the lower alkyl 7,8,9-trifluoro-1-hydroxymethyl-5-oxo-5H-thiazolo[3,2-a]quinoline-4-carboxylate (III) and corresponding carboxylic acid thereof. That is, the compound (XV) is cyclized with conc. sulfuric acid to give the compound (III) in which R is a lower alkyl, which is then hydrolyzed, preferably with sulfuric acid, to give the compound (III) in which R is hydrogen atom.

Finally the compound (III) is cyclized with a base to give the compound (II). That is, the compound (III) in which R is a lower alkyl is reacted with a tertiary amine such as triethylamine or an inorganic base such as sodium carbonate, potassium carbonate or sodium hydroxide to give the compound (II) in which R is a lower alkyl. Similarly, the compound (III) in which R is hydrogen atom is reacted with the above tertiary amine or inorganic base to give the compound (II) in which R is hydrogen atom. The compound (II) in which R is hydrogen atom can also be prepared by hydrolyzing the compound (II) in which R is a lower alkyl, preferably with sulfuric acid.

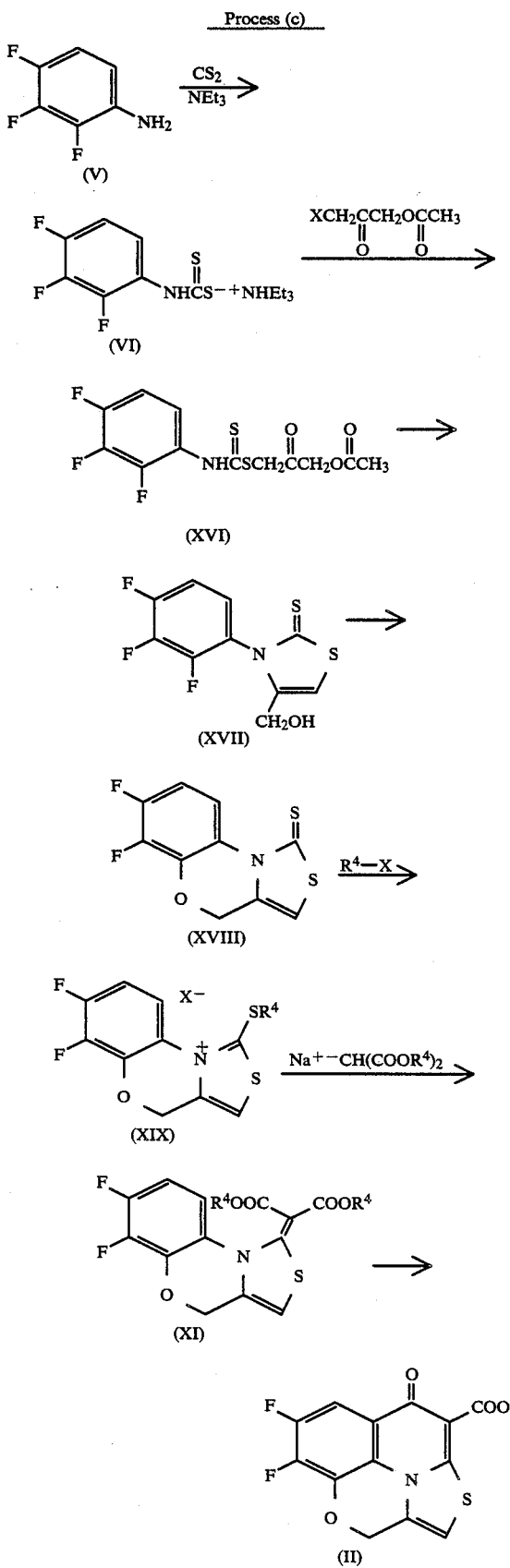

wherein R, R⁴ and X are as defined above.

That is, first the compound (VI) is obtained from the compound (V) in the same manner as in the process (a). The compound (VI) is then reacted with 1-acetoxy-3-halogenoacetone in an organic solvent such as chloroform, methylene chloride or a lower alcohol to give 3-acetoxy-2-oxopropyl N-(2,3,4-trifluorophenyl)dithiocarbamate (XVI). The compound (XVI) is then heated with an inorganic acid such as hydrochloric acid or sulfuric acid in a lower alcohol such as ethanol to give 4-hydroxymethyl-3-(2,3,4-trifluorophenyl)-2(3H)-1,3-thiazolethione (XVII). The compound (XVII) is then reacted with an inorganic base such as sodium hydride, potassium carbonate or sodium carbonate in an aprotic organic solvent such as N,N-dimethylformamide, acetonitrile or dioxane to give 6,7-difluoro-1H,4H-thiazolo[4,3-c][1,4]benzoxazine-1-thione (XVIII). The compound (XVIII) is then reacted with a lower alkyl halide such as methyl iodide or ethyl iodide in a polar organic solvent such as N,N-dimethylformamide, acetonitrile or ethanol to give 6,7-difluoro-1-alkylthio-4H-[1,4]benzoxazino[4,3-c]thiazolium halide (XIX). The compound (XIX) is then reacted with di(lower alkyl) malonate sodium salt, which is prepared from di(lower alkyl) malonate and sodium hydride, in an organic solvent such as tetrahydrofuran or dioxane to give di(lower alkyl)(6,7-difluoro-1H,4H-thiazolo[4,3-c][1,4]benzoxazin-1-ylidene)malonate (XI), which is treated in the same manner as in the process (a) to give the compound (II).

In the above process, the compound (XVII) can also be prepared from the compound (VI) directly without isolating the compound (XVI). That is, the compound (VI) is reacted with 1-acetoxy-3-halogenoacetone in an organic solvent such as acetonitrile or ethanol, followed by heating the reaction mixture with addition of hydrogen chloride to give the compound (XVII).

The compound (XI) can also be prepared from the compound (XVIII) without isolating the compound (XIX). That is, the compound (XVIII) is reacted with the lower alkyl halide such as methyl iodide or ethyl iodide in the polar solvent such as N,N-dimethylformamide, acetonitrile or ethanol, followed by the reaction with the di(lower alkyl)malonate in the presence of the base such as potassium carbonate or triethylamine to give the compound (XI).

Among the cyclic amines (ZH), an acid addition salt, for example, dihydrochloride (XX) of the compound of the formula:

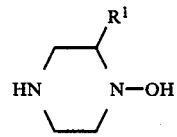

wherein R¹ is hydrogen atom or a lower alkyl can be prepared by the process as shown in the following reaction scheme:

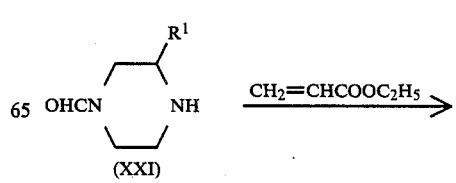

-continued $$\text{OHCN}\underset{(XXII)}{\overset{R^1}{\diagup\!\!\!\diagdown}}\text{NCH}_2\text{CH}_2\text{COOC}_2\text{H}_5 \longrightarrow$$

$$\text{OHCN}\underset{(XXIII)}{\overset{R^1}{\diagup\!\!\!\diagdown}}\text{NOH} \longrightarrow \text{HN}\underset{(XX)}{\overset{R^1}{\diagup\!\!\!\diagdown}}\text{NOH}\cdot 2\text{HCl}$$

wherein $R^1$ is as defined above.

That is, the compound (XXI) is reacted with ethyl acrylate to give the compound (XXII), which is then reacted with an oxidizing agent such as hydrogen peroxide preferably in the presence of a catalyst such as sodium tungstate to give the compound (XXIII), followed by hydrolysis of the product with hydrochloric acid to give the compound (XX).

3-Acylaminopyrrolidine such as 3-acetylamino-pyrrolidine, which is used in preparing the starting compound in the above process (C), can easily be prepared by acetylating known 1-benzyl-3-aminopyrrolidine in the conventional manner using acetic anhydride or acetyl chloride, and then hydrogenating the product to remove the benzyl group.

The compounds of the present invention show an excellent antibacterial activities with a low toxicity and are useful as an antibacterial agent.

When the compounds of the present invention are used for an antibacterial agent, they are administered to a human preferably by oral route. The dosage form for oral administration includes solid preparations such as tablets, granules, powders, fine granules and hard capsules as well as liquid preparations such as syrups and soft capsules. The pharmaceutical preparations can be prepared by the conventional procedure. Tablets, granules, powders and fine granules are prepared by mixing the compound of the present invention with conventional pharmaceutically acceptable nontoxic carriers such as lactose, starch, crystalline cellulose, magnesium stearate, talc, and the like. Hard capsules are prepared by packing the above fine granules or powders into capsules. Syrups are prepared by dissolving or suspending the compound of the present invention in an aqueous solution containing white sugar, carboxymethyl cellulose and the like. Soft capsules are prepared by dissolving or suspending the compound of the present invention in fatty diluents such as vegetable oils, oil emulsions and glycols and packing the solution or suspension into soft capsules.

The dose of the compound of the present invention, though it may vary depending on an age or a body weight of patients or severity of diseases, is generally in the range of from 0.5 to 30 mg/kg of body weight/day, preferably from 2 to 20 mg/kg of body weight/day [as the compound (I)], which may be administered once a day or may divided into 2 to 4 doses per day.

The compounds of the present invention have a wider antibacterial spectrum and potent antibacterial activities as shown in the following Experiment 1. The compounds of the present invention also show strong antibacterial activities against methicillin resistant *Staphylococcus aureus* as demonstrated in the following Experiment 2. Further, tests employing experimental animals prove that the compounds of the present invention show excellent protective effects against infection as seen in the following Experiments 3 and 4. The following Experiment 5 also proves that the compounds of the present invention have low toxicity. Consequently, it is clear that the compounds of the present invention are useful as an excellent agent for the prophylaxis and treatment of infectious diseases.

The antibacterial activities of the compounds of the present invention are tested in the following Experiments.

EXPERIMENT 1

Minimum Inhibitory Concentration (MIC)

1. Test compounds

Compound (A): 9,1-Epoxymethano-7-fluoro-8-(4-methyl-1-piperazinyl)-5-oxo-5H-thiazolo[3,2-a]quinoline-4-carboxylic acid [compound of Example 1-(a)]

Compound (B): 9,1-Epoxymethano-7-fluoro-8-(4-methyl-1-piperazinyl)-5-oxo-5H-thiazolo[3,2-a]quinoline-4-carboxylic acid.hydrochloride [compound of Example 1-(b)]

Compound (C): 9,1-Epoxymethano-7-fluoro-8-(1-piperazinyl)-5-oxo-5H-thiazolo[3,2-a]quinoline-4-carboxylic acid [compound of Example 2-(a)]

Compound (D): 9,1-Epoxymethano-7-fluoro-8-(1-piperazinyl)-5-oxo-5H-thiazolo[3,2-a]quinoline-4-carboxylic acid.hydrochloride.½ hydrate [compound of Example 2-(b)]

Compound (E): 9,1-Epoxymethano-7-fluoro-8-(3-methyl-1-piperazinyl)-5-oxo-5H-thiazolo[3,2-a]quinoline-4-carboxylic acid.¼ hydrate (compound of Example 3)

Compound (F): 9,1-Epoxymethano-7-fluoro-8-(4-hydroxy-1-piperazinyl)-5-oxo-5H-thiazolo[3,2-a]quinoline-4-carboxylic acid.¼ hydrate (compound of Example 4)

Compound (G): 9,1-Epoxymethano-7-fluoro-8-(1-pyrrolidinyl)-5-oxo-5H-thiazolo[3,2-a]quinoline-4-carboxylic acid (compound of Example 5)

Compound (H): 9,1-Epoxymethano-7-fluoro-8-(3-hydroxy-1-pyrrolidinyl)-5-oxo-5H-thiazolo[3,2-a]quinoline-4-carboxylic acid (compound of Example 6)

Compound (I): 9,1-Epoxymethano-7-fluoro-8-(3-amino-1-pyrrolidinyl)-5-oxo-5H-thiazolo[3,2-a]quinoline-4-carboxylic acid (compound of Example 7)

Compound (J): 9,1-Epoxymethano-7-fluoro-8-(4-ethyl-1-piperazinyl)-5-oxo-5H-thiazolo[3,2-a]quinoline-4-carboxylic acid.hydrochloride.½ hydrate [compound of Example 10-(b)]

OFLOXACIN (control)

2. Method

The compounds of the present invention (A, C, E, F, G, H and I) and ofloxacin as control were dissolved in 0.1N aqueous potassium hydroxide to prepare a solution of 5000 μg/ml in concentration. The compounds of the present invention (B, D and J) were dissolved in sterilized distilled water to prepare a solution of 5000 μg/ml in concentration. Each solution was diluted with sterilized distilled water to prepare a standard solution with a concentration of each test compound: 1000 μg/ml. The test was carried out by a method as approved by Japan Society of Chemotherapy [cf. Chemotherapy, 29, 76–79 (1981) (Tokyo)].

3. Results

The test results are shown in Table 1.

lated a range of MIC (MIC$_{range}$) of the test compound against these resistant strains, a minimum concentration for inhibiting the growth of the strains by 50% (MIC$_{50}$)

TABLE 1

| | | Minimum inhibitory concentration (MIC: μg/ml) | | | | | | | | | | |
| | | Compounds of the present invention | | | | | | | | | | Ofloxa- |
| | Gram | A | B | C | D | E | F | G | H | I | J | cin |
|---|---|---|---|---|---|---|---|---|---|---|---|---|
| *Staphylococcus aureus* FDA 209P JC-1 | + | 0.20 | 0.20 | 0.39 | 0.39 | 0.20 | 0.39 | 0.025 | 0.025 | 0.20 | 0.20 | 0.39 |
| *Staphylococcus aureus* IID 803 | + | 0.20 | 0.20 | 0.39 | 0.39 | 0.20 | 0.39 | 0.05 | 0.025 | 0.39 | 0.20 | 0.39 |
| *Staphylococcus epidermidis* IAM-1296 | + | 0.39 | 0.39 | 0.78 | 1.56 | 0.78 | 1.56 | 0.05 | 0.20 | 0.78 | 0.39 | 0.78 |
| *Streptococcus faecalis* IID 682 | + | 0.39 | 0.78 | 0.78 | 0.78 | 0.78 | 1.56 | 0.20 | 0.20 | 0.78 | 0.78 | 1.56 |
| *Bacillus subtilis* ATCC 6633 | + | 0.10 | 0.10 | 0.20 | 0.20 | 0.10 | 0.10 | 0.025 | 0.006 | 0.20 | 0.10 | 0.10 |
| *Micrococcus luteus* ATCC 9341 | + | 1.56 | 1.56 | 3.13 | 3.13 | 3.13 | 6.25 | 3.13 | 0.78 | 1.56 | 3.13 | 3.13 |
| *Escherichia coli* NIHJ JC-2 | − | 0.10 | 0.10 | 0.10 | 0.10 | 0.20 | 0.20 | 0.20 | 0.05 | 0.20 | 0.10 | 0.10 |
| *Escherichia coli* KC-14 | − | 0.10 | 0.10 | 0.10 | 0.10 | 0.10 | 0.10 | 0.20 | 0.05 | 0.10 | 0.10 | 0.10 |
| *Klebsiella pneumoniae* PCI 602 | − | 0.025 | 0.025 | 0.05 | 0.025 | 0.025 | 0.025 | 0.10 | 0.006 | 0.05 | 0.025 | 0.05 |
| *Salmonella typhimurium* IID 971 | − | 0.05 | 0.05 | 0.05 | 0.10 | 0.10 | 0.05 | 0.10 | 0.0125 | 0.10 | 0.05 | 0.05 |
| *Shigella sonnei* EW-33 | − | 0.05 | 0.05 | 0.05 | 0.05 | 0.10 | 0.05 | 0.10 | 0.05 | 0.10 | 0.10 | 0.05 |
| *Serratia marcescens* IAM 1184 | − | 0.20 | 0.39 | 0.39 | 0.39 | 0.39 | 0.78 | 1.56 | 0.39 | 0.78 | 0.39 | 0.78 |
| *Pseudomonas aeruginosa* IFO 3445 | − | 0.78 | 1.56 | 0.78 | 0.78 | 1.56 | 1.56 | 1.56 | 0.39 | 0.78 | 3.13 | 1.56 |
| *Pseudomonas aeruginosa* E-2 | − | 0.78 | 0.78 | 0.78 | 0.78 | 0.78 | 1.56 | 1.56 | 0.39 | 0.78 | 1.56 | 1.56 |
| *Pseudomonas aeruginosa* NCTC 10490 | − | 0.78 | 0.78 | 0.39 | 0.78 | 0.78 | 0.78 | 0.78 | 0.39 | 0.39 | 0.78 | 1.56 |
| *Morganella morganii* IFO 3848 | − | 0.10 | 0.10 | 0.10 | 0.10 | 0.10 | 0.10 | 0.20 | 0.10 | 0.20 | 0.10 | 0.10 |
| *Proteus vulgaris* OX-19 | − | 0.05 | 0.05 | 0.10 | 0.10 | 0.05 | 0.05 | 0.10 | 0.0125 | 0.20 | 0.05 | 0.05 |
| *Proteus mirabilis* IFO 3849 | − | 0.20 | 0.20 | 0.20 | 0.20 | 0.20 | 0.20 | 0.39 | 0.10 | 0.39 | 0.39 | 0.39 |
| *Enterobacter aerogenes* ATCC 13048 | − | 0.10 | 0.10 | 0.10 | 0.20 | 0.10 | 0.10 | 0.10 | 0.10 | 0.10 | 0.10 | |
| *Enterobacter cloacae* 963 | − | 0.10 | 0.10 | 0.20 | 0.20 | 0.20 | 0.20 | 0.39 | 0.10 | 0.20 | 0.10 | 0.20 |
| *Citrobacter freundii* NIHJ 10018-68 | − | 0.20 | 0.20 | 0.20 | 0.20 | 0.78 | 0.20 | 3.13 | 0.39 | 0.20 | 0.39 | 0.39 |
| *Acinetobacter calcoaceticus* Ac 54 | − | 0.20 | 0.20 | 0.78 | 1.56 | 0.78 | 1.56 | 0.20 | 0.10 | 0.78 | 0.10 | 0.39 |

EXPERIMENT 2

Minimum Inhibitory Concentration Against Clinically Isolated Methicillin Resistant *Staphylococcus aureus*

1. Test compounds

Compound (B): 9,1-Epoxymethano-7-fluoro-8-(4-methyl-1-piperazinyl)-5-oxo-5H-thiazolo[3,2-a]quinoline-4-carboxylic acid.hydrochloride [compound of Example 1-(b)]

OFLOXACIN (control)

2. Method

The compound (B) was dissolved in sterilized distilled water, and ofloxacin in 0.1N aqueous potassium hydroxide, to prepare a solution of 5000 μg/ml in concentration each. The above solutions were then diluted with sterilized distilled water to prepare a standard solution with a concentration of the test compound: 1000 μg/ml each. The test was carried out by a method approved by Japan Society of Chemotherapy (ibidem) to measure minimum inhibitory concentration (MIC) against 54 strains of clinically isolated methicillin resistant *Staphylococcus aureus*, from which there was calculated a minimum concentration for inhibiting the growth of the strains by 90% (MIC$_{90}$).

3. Results

The test results are shown in Table 2.

TABLE 2

| Test compounds | MIC$_{range}$ (μg/ml) | MIC$_{50}$ (μg/ml) | MIC$_{90}$ (μg/ml) |
|---|---|---|---|
| Compound (B) | 0.10–0.39 | 0.20 | 0.20 |
| Ofloxacin | 0.39–1.56 | 0.39 | 1.56 |

EXPERIMENT 3

Effect on Treatment of General Infectious Disease

1. Test compounds

The same as in the Experiment 2.

2. Test microorganisms and inoculum size

*Staphylococcus aureus* IID 803 (1.0 × 10$^6$ CFU/mouse)
*Escherichia coli* KC-14 (1.2 × 10$^4$ CFU/mouse)
*Pseudomonas aeruginosa* E-2 (1.6 × 10$^4$ CFU/mouse)

3. Method

The test microorganisms were subjected to standing culture in Trypto-Soya Agar "Nissui" (made by Nissui Seiyaku K.K., Japan) at 37° C. for 16 to 18 hours. The culture was then diluted with PBS (Dulbecco's phosphate buffered saline) and mixed with an equivalent amount of 10% (w/v) Mucin (Bacto Mucin Bacteriological, made by Difco Co.) to prepare a microorganism solution. The thus prepared microorganism solution (0.5 ml each) was intraperitoneally innoculated to ddY male mice (4 weeks age, weighing 20–22 g, 5 mice in each group), to infect the animals. One hour after the infection, the compound (B) of the present invention dissolved in sterilized distilled water or ofloxacin suspended in 0.5% (w/v) aqueous sodium carboxymethyl cellulose solution was orally administered to mice.

The mice were daily observed for one week, and from the survival number of mice after one week, the 50% effective dose ($ED_{50}$) was calculated by Weil method.

4. Results

The test results are shown in Table 3.

TABLE 3

| Test microorganism | $ED_{50}$ (mg/kg) Compound (B) | Ofloxacin |
|---|---|---|
| S. aureus IID 803 | 8.1 | 11.5 |
| E. coli KC-14 | 1.0 | 1.1 |
| P. aeruginosa E-2 | 17.7 | 22.9 |

EXPERIMENT 4

Effect on Treatment of Infectiousness of the Genito-Urinary Tract

1. Test Compound

The same as in the Experiment 2.

2. Test microorganism and inoculum size

E. coli KC-14 ($5.6 \times 10^5$ CFU/mouse)

3. Method

A microorganism solution (0.1 ml) prepared in the same manner as described in Experiment 3 was introduced into urinary bladder through urinary tract of ICR female mice (5 weeks age, weighing 20 to 22 g, 5 mice in each group), and then urinary meatus was clasped with clip for 4 hours to infect the animals. After taking off the clip, the compound (B) of the present invention dissolved in sterilized distilled water or ofloxacin suspended in 0.5% aqueous sodium carboxymethyl cellulose solution was orally administered to mice. Two days after the infection, mice kidneys were taken out and weighed, to which PBS (Dulbecco's phosphate buffered saline) was added and the mixture was homogenized. The homogenate was then diluted with PBS and inoculated onto a plate of modified Drigalski Agar (BTB lactose agar "Nissui", made by Nissui Seiyaku K.K., Japan) and cultured at 37° C. for 18 hours. The number of the colonies of infectious bacteria grown on the plate was counted. The number of living bacteria per 1 g of kidney was calculated from the number of colonies and the kidney weight. The living bacteria number/1 g of kidney of not more than $10^4$ was regarded as effective and an effective dose for 50% mice ($ED_{50}$) was calculated by Weil method.

4. Results

The test results are shown in Table 4.

TABLE 4

| Test compounds | $ED_{50}$ (mg/kg) |
|---|---|
| Compound (B) | 21.7 |
| Ofloxacin | 50.0 |

EXPERIMENT 5

Acute Toxicity ($LD_{50}$)

1. Method

The compound (B) of the present invention was dissolved in sterilized distilled water and the solution was orally administered to ddY male mice (5 weeks age, weighing 20 to 25 g, 5 mice in each group), which had been fasted for 18 hours. After that, mice was observed for the number of deaths and an acute toxicity ($LD_{50}$) was calculated by Weil method.

2. Results

The compound (B) of the present invention proved to have a $LD_{50}$ value of 1231 mg/kg.

The preparation of the compound of the present invention is illustrated by means of the following Reference Examples and Examples, but should not be construed to be limited thereto.

REFERENCE EXAMPLE 1

Preparation of triethylammonium N-(2,3,4-trifluorophenyl)dithiocarbamate [compound (VI)]

To 2,3,4-trifluoroaniline (48.8 g) were added triethylamine (100.7 g) and carbon disulfide (30.3 g) and the mixture was stirred at room temperature for 1 week. Precipitated crystals were filtered and washed with ether to give the title compound (95.4 g) as orange-colored crystals, which was then recrystallized from a mixed solvent of ethermethylene chloride to give colorless crystals.

NMR (CDCl$_3$) δ: 1.4 (9H, t, J=7 Hz), 3.3 (6H, q, J=7 Hz), 6.6–7.2 (1H, m), 7.6–8.2 (1H, m), 8.1–8.7 (1H, bs), 8.5–9.4 (1H, bs).

IR (KBr) $\gamma_{max}$ cm$^{-1}$: 3108, 2904, 2588, 2466, 1513, 1494, 1263, 1242, 1056, 1009.

REFERENCE EXAMPLE 2

Preparation of 2,3,4-trifluorophenyl isothiocyanate [compound (VII)]

Triethylammonium N-(2,3,4-trifluorophenyl)dithiocarbamate (92.0 g) and triethylamine (31.5 g) were added to chloroform (360 ml) and thereto ethyl chlorocarbonate (33.8 g) was added dropwise at 2°–6° C. with stirring over a period of 1 hour. The mixture was stirred for 10 minutes and washed with 3N hydrochloric acid and then with water. The organic layer was dried over anhydrous magnesium sulfate and the solvent was distilled off under reduced pressure. The obtained residue ws purified by silica-gel column chromatography (Silica gel 60, 230–400 mesh, made by Merck Co., 220 g, eluent: hexane) under medium pressure, followed by distillation under reduced pressure to give the title compound (42.0 g) as colorless liquid, b.p.: 96°–97° C./17 mmHg.

NMR (CDCl$_3$) δ: 6.6–7.3 (m).

IR (neat) $\gamma_{max}$ cm$^{-1}$: 2018, 1612, 1512, 1327, 1276, 1242, 1173, 1060, 1006.

REFERENCE EXAMPLE 3

Preparation of diethyl [(2,3,4-trifluoroanilino)(mercapto)methylene]malonate sodium salt [compound (VIII) in which R$^4$ is ethyl]

Diethyl malonate (34.4 g) was added dropwise to a suspension of sodium hydride (8.6 g, in oil, content: 60 w/w %) in tetrahydrofuran (250 ml) with stirring while maintaining the internal temperature at 5°–10° C. over a period of 40 minutes. Ten minutes after the dropwise addition, 2,3,4-trifluorophenyl isothiocyanate (40.5 g) was added dropwise at the same temperature over a period of 40 minutes. The mixture was stirred at room temperature for 1 hour and 45 minutes and the reaction mixture was evaporated to dryness under reduced pressure. The residue was washed with ether to give the title compound (78.5 g) as colorless crystals.

NMR (DMSO-d$_6$) δ: 1.1 (6H, t, J=7 Hz), 4.0 (4H, q, J=7 Hz), 7.1–7.2 (1H, m), 8.5–8.6 (1H, m), 11.8 (1H, s).

REFERENCE EXAMPLE 4

Preparation of diethyl [(2,3,4-trifluoroanilino)(3-acetoxy-2-oxopropylthio)methylene]malonate [compound (IX) in which R$^4$ is ethyl]

Diethyl [(2,3,4-trifluoroanilino)(mercapto)methylene]malonate sodium salt (5.3 g) was dissolved in N,N-dimethylformamide (70 ml) and thereto 1-acetoxy-3-chloroacetone (2.2 g) was added and the mixture was stirred at room temperature for 30 minutes. The reaction mixture was filtered to remove insoluble materials. After the filtrate was evaporated to dryness under reduced pressure, water was added to the residue and the mixture was extracted with chloroform. The extract was washed with a NaCl solution and dried over anhydrous magnesium sulfate, followed by distilling off the solvent under reduced pressure to give the title compound (6.0 g) as pale yellow oil.

Mass spectrum (m/e): 463 (M+).

REFERENCE EXAMPLE 5

Preparation of diethyl [3-(2,3,4-trifluorophenyl)-4-hydroxymethyl-2-thiazolidene]malonate [compound (X) in which R$^4$ is ethyl]

Conc. sulfuric acid (5 ml) was added to diethyl [(2,3,4-trifluoroanilino)(3-acetoxy-2-oxopropylthio)methylene]malonate (3.8 g) and the mixture was stirred at room temperature for 30 minutes. After a piece of ice (4 g) was added and the mixture was stirred for 1 hour, cold water was added thereto and the mixture was extracted with chloroform. The extract was washed with a NaCl solution and dried over anhydrous magnesium sulfate and the solvent was distilled off under reduced pressure. The residue was recrystallized from a mixed solvent of hexane-ethyl acetate to give the title compound (2.2 g) as colorless crystals, m.p. 142°–145° C.

Elementary analysis for C$_{17}$H$_{16}$NO$_5$SF$_3$: Calcd. (%): C, 50.62; H, 4.00; N, 3.47. Found (%): C, 50.67; H, 3.98; N, 3.30.

REFERENCE EXAMPLE 6

Preparation of diethyl 6,7-difluoro-1H,4H-thiazolo[4,3-c][1,4]benzoxazin-1-ylidene)malonate [compound (XI) in which R$^4$ is ethyl]

Diethyl [3-(2,3,4-trifluorophenyl)-4-hydroxymethyl-2-thiazolidene]malonate (2.0 g) was dissolved in dioxane (60 ml) and thereto sodium hydride (0.2 g in oil, content: 60 w/w %) was added and the mixture was stirred at room temperature for 20 minutes and then refluxed for 10 minutes. The reaction mixture was evaporated to dryness under reduced pressure. To the residue was added water and the mixture was extracted with chloroform. The extract was washed with a NaCl solution and dried over anhydrous magnesium sulfate, followed by distilling off the solvent. The obtained residue was recrystallized from a mixed solvent of hexane-ethyl acetate to give the title compound (1.4 g) as pale yellow crystals, m.p. 161°–164° C.

Elementary analysis for C$_{17}$H$_{15}$NO$_5$SF$_2$: Calcd. (%): C, 53.26; H, 3.94; N, 3.65. Found (%): C, 53.32; H, 3.84; N, 3.54.

REFERENCE EXAMPLE 7

Preparation of ethyl 9,1-epoxymethano-7,8-difluoro-5-oxo-5H-thiazolo[3,2-a]quinoline-4-carboxylate [compound (II) in which R is ethyl]

A mixture of diethyl (6,7-difluoro-1H,4H-thiazolo[4,3-c][1,4]beonzoxazin-1-ylidene)malonate (1.0 g) and ethyl polyphosphate (10 g) was stirred at 138° C. for 1.5 hour. After stirring, cold water was added to the reaction mixture and the mixture was extracted with chloroform. The extract was washed with a NaCl solution and dried over magnesium sulfate, followed by distilling off the solvent under reduced pressure. The residue was washed with ether to give the title compound (0.54 g) as colorless crystals, which was recrystallized from N,N-dimethylformamide, m.p.>300° C.

NMR (DMSO-d$_6$) δ: 1.3 (3H, t, J=7 Hz), 4.3 (2H, q, J=7 Hz), 5.6 (2H, d, J=1 Hz), 7.5 (1H, t, J=1 Hz), 7.6 (1H, dd, J=11 Hz, 8 Hz).

IR (KBr) $\gamma_{max}$ cm$^{-1}$: 3078, 1662, 1583, 1506, 1469.

Elementary analysis for C$_{15}$H$_9$NO$_4$SF$_2$: Calcd. (%): C, 53.41; H, 2.69; N, 4.15. Found (%): C, 53.52; H, 2.71; N, 4.01.

REFERENCE EXAMPLE 8

Preparation of 9,1-epoxymethano-7,8-difluoro-5-oxo-5H-thiazolo[3,2-a]quinoline-4-carboxylic acid [compound (II) in which R is hydrogen atom]

Concd. sulfuric acid (13.5 ml) was added to ethyl 9,1-epoxymethano-7,8-difluoro-5-oxo-5H-thiazolo[3,2-a]quinoline-4-carboxylate (1.23 g) and the mixture was stirred at 85° C. for 10 hours. After stirring, a piece of ice was added to the reaction mixture and the resulting precipitate was filtered and washed with water to give colorless powder (1.11 g), which was then recrystallized from dimethyl sulfoxide to give the title compound (0.63 g), m.p. 288° C. (dec.).

NMR (DMSO-d$_6$) δ: 5.7 (2H, d, J=1 Hz), 7.7 (1H, t, J=1 Hz), 7.9 (1H, dd, J=11 Hz, 7 Hz), 15.3 (1H, s).

IR (KBr) $\gamma_{max}$ cm$^{-1}$: 3062, 1963, 1505, 1479.

Elementary analysis for $C_{13}H_5NO_4SF_2$: Calcd. (%): C, 50.49; H, 1.63; N, 4.53. Found (%): C, 50.23; H, 1.65; N, 4.28.

REFERENCE EXAMPLE 9

Preparation of diethyl [(2,3,4-trifluoroanilino)(p-methoxybenzylthio)methylene]malonate [compound (XII) in which $R^4$ is ethyl]

Diethyl [(2,3,4-trifluoroanilino)(mercapto)methylene]malonate sodium salt (68.5 g) was dissolved in N,N-dimethylformamide (200 ml) and thereto p-methoxybenzyl chloride (28.9 g) was added dropwise at 3° to 5° C. over a period of 5 minutes. After the reaction mixture was stirred at room temperature for 1 hour and evaporated to dryness under reduced pressure, water was added to the residue and the mixture was extracted with chloroform. After the extract was washed with a NaCl solution and dried over magnesium sulfate, the solvent was distilled off under reduced pressure to give the title compound (82.9 g) as colorless solid, which was then recrystallized from a mixed solvent of haxane-benzene.

IR (KBr) $\gamma_{max}$ cm$^{-1}$: 1720, 1663, 1581, 1515. Elementary analysis for $C_{22}H_{22}NO_5SF_3$: Calcd. (%): C, 56.28; H, 4.72; N, 2.98. Found (%): C, 56.19; H, 4.58; N, 3.06.

REFERENCE EXAMPLE 10

Preparation of ethyl 4-hydroxy-6,7,8-trifluoro-2-(p-methoxybenzylthio)-quinoline-3-carboxylate [compound (XIII) in which $R^4$ is ethyl]

A solution of diethyl [(2,3,4-trifluoroanilino)(p-methoxybenzylthio)methylene]malonate (80.9 g) in diphenyl ether (60 ml) heated at 110° C. was added dropwise to diphenyl ether (210 ml) kept at 250° to 260° C. with stirring under nitrogen stream over a period of 15 minutes. After the reaction mixture was further stirred at the same temperature for 5 minutes, the mixture was cooled to room temperature and added to hexane (3000 ml). The resulting precipitate was filtered to give the title compound (59.9 g), which was recrystallized from ethyl acetate to give yellow crystals, m.p. 174°–176° C.

Elementary analysis for $C_{20}H_{16}NO_4SF_3$: Calcd. (%): C, 56.73; H, 3.81; N, 3.31. Found (%): C, 56.88; H, 3.81; N, 3.28.

REFERENCE EXAMPLE 11

Preparation of ethyl 4-hydroxy-2-mercapto-6,7,8-trifluoroquinoline-3-carboxylate [compound (XIV) in which $R^4$ is ethyl]

Ethyl 4-hydroxy-6,7,8-trifluoro-2-(p-methoxybenzylthio)quinoline-3-carboxylate (59.9 g) was added to a mixture of trifluoroacetic acid (500 g), trifluoromethanesulfonic acid (100 g) and anisole (92.5 g) at −23° to −20° C. with stirring over a period of 15 minutes. The mixture was stirred at −20° to −15° C. for 30 minutes and then at room temperature for 1.5 hour. After the reaction mixture was concentrated under reduced pressure, a piece of ice was added to the concentrate and the mixture was made alkaline with 10% aqueous sodium hydroxide. After insoluble materials were removed by filtration, the filtrate was washed with ether and made strongly acidic with concd. hydrochloric acid. The resulting powder was filtered to give the title compound (33 g), which was recrystallized from ethanol to give yellow crystals, m.p. 190° C. (dec.).

Elementary analysis for $C_{12}H_8NO_3SF_3$: Calcd. (%): C, 47.53; H, 2.66; N, 4.62. Found (%): C, 47.59; H, 2.66; N, 4.66.

REFERENCE EXAMPLE 12

Preparation of ethyl 2-(3-acetoxy-2-oxopropylthio)-6,7,8-trifluoro-4-hydroxyquinoline-3-carboxylate [compound (XV) in which $R^4$ is ethyl]

To methylene chloride (500 ml) were added ethyl 4-hydroxy-2-mercapto-6,7,8-trifluoroquinoline-3-carboxylate (33 g), triethylamine (22 g) and 1-acetoxy-3-chloroacetone (16.4 g) and the mixture was stirred at room temperature for 15 minutes. Chloroform (700 ml) was added to the reaction solution and washed with 0.1N hydrochloric acid, water and a NaCl solution in this order, dried over anhydrous magnesium sulfate and evaporated to dryness under reduced pressure. The residue was recrystallized from ethyl acetate to give the title compound (37.2 g) as colorless crystals, m.p. 175°–180° C.

Elementary analysis for $C_{17}H_{14}NO_6SF_3$: Calcd. (%): C, 48,92; H, 3.38; N, 3.36. Found (%): C, 48.98; H, 3.38; N, 3.36.

REFERENCE EXAMPLE 13

Preparation of ethyl 7,8,9-trifluoro-1-hydroxymethyl-5-oxo-5H-thiazolo[3,2-a]quinoline-4-carboxylate [compound (III) in which R is ethyl]

Ethyl 2-(3-acetoxy-2-oxopropylthio)-6,7,8-trifluoro-4-hydroxyquinoline-3-carboxylate (3.54 g) was added to concd. sulfuric acid (35 ml) and the mixture was stirred at room temperature for 2 hours and 15 minutes. Thereto water (29 ml) was added gradually with ice-cooling and the mixture was stirred at room temperature for 26 hours, followed by addition of ice-water (400 ml). After precipitated crystal was filtered and washed with water, the resultant was recrystallized from a mixed solvent of chloroform-ethanol to give the title compound (2.38 g) as pale yellow crystals.

NMR (CDCl$_3$) δ: 1.4 (3H, t, J=7 Hz), 4.3 (2H, q, J=7 Hz), 5.0 (2H, dd, J=1 Hz, 6.5 Hz), 7.2 (1H, t, J=1 Hz), 7.8 (1H, ddd, J=2 Hz, 8 Hz, 10 Hz).

IR (KBr) $\gamma_{max}$ cm$^{-1}$: 3254, 3088, 1676, 1596, 1570, 1525, 1456.

Elementary analysis for $C_{15}H_{10}NO_4SF_3$: Calcd. (%): C, 50.42; H, 2.82; N, 3.92. Found (%): C, 50.45; H, 2.86; N, 3.84.

REFERENCE EXAMPLE 14

Preparation of 7,8,9-trifluoro-1-hydroxymethyl-5-oxo-5H-thiazolo[3,2-a]quinoline-4-carboxylic acid [compound (III) in which R is hydrogen atom]

Concd. sulfuric acid (300 ml) was added to ethyl 2-(3-acetoxy-2-oxopropylthio)-6,7,8-trifluoro-4-hydroxyquinoline-3-carboxylate (36.0 g) and the mixture was stirred at room temperature for 45 minutes and then at 85° C. for 19 hours. After adding ice-water (250 g) with cooling, the mixture was stirred at room temperature for 3 hours and the reaction mixture was then poured into ice-water. After precipitated crystal was filtered and washed with water, the resultant was recrystallized from a mixed solvent of chloroform-methanol to give the title compound (14.2 g) as light brown crystals, m.p. 220° C. (dec.).

NMR (DMSO-d$_6$) δ: 4.8–5.0 (2H, m), 5.7 (1H, t, J=5 Hz), 7.8 (1H, t, J=1 Hz), 8.2 (1H, ddd, J=2 Hz, 8 Hz, 10 Hz), 15.3 (1H, s).

IR (KBr) $\gamma_{max}$ cm$^{-1}$: 3110, 3070, 1675, 1497, 1468.

Elementary analysis for $C_{13}H_6NO_4SF_3$: Calcd. (%): C, 47.42; H, 1.84; N, 4.25. Found (%): C, 47.38; H, 1.72; N, 4.34.

REFERENCE EXAMPLE 15

Preparation of ethyl 9,1-epoxymethano-7,8-difluoro-5-oxo-5H-thiazolo[3,2-a]quinoline-4-carboxylate [compound (II) in which R is ethyl]

Ethyl 7,8,9-trifluoro-1-hydroxymethyl-5-oxo-5H-thiazolo[3,2-a]quinoline-4-carboxylate (0.50 g) prepared in Reference Example 13 and triethylamine (0.40 g) were added to dimethylsulfoxide (15 ml) and the mixture was stirred at 75° C. for 1 hour and 30 minutes. After the reaction mixture was added to ice-water and insoluble substance was filtered, the resultant was washed with water and then with ethanol, followed by recrystallization from a mixed solvent of chloroform-ethanol to give the title compound (0.42 g) as colorless crystals. The compound thus prepared had physical properties identical to those of ethyl 9,1-epoxymethano-7,8-difluoro-5-oxo-5H-thiazolo[3,2-a]quinoline-4-carboxylate prepared in Reference Example 7.

REFERENCE EXAMPLE 16

Preparation of 9,1-epoxymethano-7,8-difluoro-5-oxo-5H-thiazolo[3,2-a]quinoline-4-carboxylic acid [compound (II) in which R is hydrogen atom]

7,8,9-Trifluoro-1-hydroxymethyl-5-oxo-5H-thiazolo[3,2-a]quinoline-4-carboxylic acid (0.33 g) prepared in Reference Example 14 and potassium carbonate (0.42 g) were added to N,N-dimethylformamide (7 ml) and the mixture was stirred at 45° C. for 1 hour and 45 minutes. To the reaction mixture was added water (110 ml) and insoluble substance was filtered off and the filtrate was made acidic by adding acetic acid. The resulting precipitate was filtered and washed with water to give crude title compound (0.26 g), which was then recrystallized from dimethylsulfoxide to give the title compound (0.15 g). The compound thus prepared had physical properties identical to those of 9,1-epoxymethano-7,8-difluoro-5-oxo-5H-thiazolo[3,2-a]quinoline-4-carboxylic acid prepared in Reference Example 8.

The title compound could also be prepared in the following manner by employing sodium hydroxide in place of potassium carbonate. That is, 7,8,9-trifluoro-1-hydroxymethyl-5-oxo-5H-thiazolo[3,2-a]quinoline-4-carboxylic acid (0.17 g) was added to 0.5N aqueous sodium hydroxide solution (5 ml) and the mixture was stirred at room temperature for 1 hour. The reaction solution was made acidic by adding acetic acid. The resulting precipitate was filtered and washed with water to give crude title compound (0.13 g), which was then recrystallized in the same manner as above to give the title compound (60 mg). The compound thus prepared had also physical properties identical to those of 9,1-epoxymethano-7,8-difluoro-5-oxo-5H-thiazolo[3,2-a]quinoline-4-carboxylic acid prepared in Reference Example 8.

REFERENCE EXAMPLE 17

Preparation of 3-acetoxy-2-oxopropyl N-(2,3,4-trifluorophenyl)dithiocarbamate [compound (XVI)]

Triethylammonium N-(2,3,4-trifluorophenyl)dithiocarbamate (2.15 g) prepared in the same manner as in Reference Example 1 was added to methylene chloride (30 ml) and thereto 1-acetoxy-3-chloroacetone (1.0 g) was added dropwise at 2° to 7° C. with stirring over a period of 10 minutes. The mixture was stirred for 20 minutes and washed with 3N hydrochloric acid and then with water. The organic layer was dried over anhydrous magnesium sulfate and then the solvent was distilled off under reduced pressure. The residue was recrystallized from a mixed solvent of hexane-ethyl acetate to give the title compound (1.43 g) as colorless crystals.

IR (KBr) $\gamma_{max}$ cm$^{-1}$: 3286, 1751, 1512, 1500, 1240, 1042, 1031.

Mass spectrum (m/e): 337 (M+).

REFERENCE EXAMPLE 18

Preparation of 4-hydroxymethyl-3-(2,3,4-trifluorophenyl)-2(3H)-thiazolethione [compound (XVII)]

3-Acetoxy-2-oxopropyl N-(2,3,4-trifluorophenyl)dithiocarbamate (1.0 g) prepared in the previous Reference Example was added to ethanol (15 ml) and thereto 10% solution of hydrogen chloride in ethanol (5 ml) was added and the mixture was refluxed for one hour and 30 minutes. After the solvent was distilled off under reduced pressure, cooled water was added to the residue and the resultant was extracted with chloroform. After the extract was washed with a NaCl solution and dried over anhydrous magnesium sulfate, the solvent was distilled off under reduced pressure. The residue was recrystallized from a mixed solvent of hexane-ethyl acetate to give the title compound (0.56 g) as pale yellow crystals, m.p. 113°–116° C.

NMR (CDCl$_3$) δ: 1.9 (1H, t, J=6 Hz), 4.3 (2H, m), 6.7 (1H, s), 7.0–7.2 (2H, m).

IR (KBr) $\gamma_{max}$ cm$^{-1}$: 3432, 1514, 1506, 1308, 1292, 1268, 1034.

Elementary analysis for $C_{10}H_6NOS_2F_3$: Calcd. (%): C, 43.31; H, 2.18; N, 5.05. Found (%): C, 43.38; H, 2.25; N, 4.78.

REFERENCE EXAMPLE 19

Preparation of 4-hydroxymethyl-3-(2,3,4-trifluorophenyl)-2(3H)-thiazolethione [compound (XVII)]

Triethylammonium N-(2,3,4-trifluorophenyl)dithiocarbamate (81.2 g) prepared in the same manner as in Reference Example 1 was added to ethanol (800 ml) and thereto 1-acetoxy-3-chloroacetone (37.7 g) was added dropwise at 5° to 7° C. with stirring over a period of 20 minutes. After stirring the mixture for 50 minutes, 10% solution of hydrogen chloride in ethanol (240 ml) was added and the mixture was refluxed for 3 hours. After the solvent was distilled off under the reduced pressure, cooled water was added to the residue and resultant was extracted with chloroform. The extract was washed with a NaCl solution and dried over anhydrous sodium sulfate, followed by distilling off the solvent under reduced pressure. The residue was recrystallized from a mixed solvent of hexane-ethyl acetate to give the title compound (59 g) as pale yellow crystals. The compound had physical properties identical to those of 4-hydroxymethyl-3-(2,3,4-trifluorophenyl)-2(3H)-thiazolethione prepared in the above Reference Example 18.

REFERENCE EXAMPLE 20

Preparation of 6,7-difluoro-1H,4H-thiazolo[4,3-c][1,4]benzoxazine-1-thione [compound (XVIII)]

4-Hydroxymethyl-3-(2,3,4-trifluorophenyl)-2(3H)-thiazolethione (60 g) prepared in the same manner as in Reference Example 19 was dissolved in N,N-dimethylformamide (450 ml) and thereto potassium carbonate (60 g) was added and the mixture was stirred at 110° C. for 3 hours. After the reaction mixture was evaporated to dryness, water was added to the residue and the resultant was extracted with chloroform. The extract was washed with a NaCl solution and dried over anhydrous sodium sulfate, followed by distilling off the solvent under reduced pressure. The residue was recrystallized from a mixed solvent of hexane-ethyl acetate to give the title compound (51 g) as pale yellow crystals, m.p. 163°–167° C.

NMR (CDCl$_3$) δ: 5.0 (2H, d, J=1 Hz), 6.6 (1H, t, J=1 Hz), 7.0 (1H, dt, J=8 Hz, 9.5 Hz), 9.5 (1H, ddd, J=2.5 Hz, 4.5 Hz, 9.5 Hz).

IR (KBr) γ$_{max}$ cm$^{-1}$: 1514, 1488, 1282, 1262, 1058.

Elementary analysis for C$_{10}$H$_5$NOS$_2$F$_2$: Calcd. (%): C, 46.69; H, 1.96; N, 5.44. Found (%): C, 46.83; H, 2.03; N, 5.49.

REFERENCE EXAMPLE 21

Preparation of 6,7-difluoro-1-methylthio-4H-[1,4]benzoxazino[4,3-c]thiazolinium iodide [compound (XIX) in which R$^4$ is methyl and X is iodine atom]:

6,7-Difluoro-1H,4H-thiazolo[4,3-c][1,4]benzoxazine-1-thione (60 g) prepared in the same manner as in Reference Example 20 and methyl iodide (66 g) were dissolved in N,N-dimethylformamide (300 ml) and the mixture was stirred at room temperature for 34 hours. The precipitate was filtered and washed with acetonitrile to give the title compound (80.4 g) as yellow crystals.

NMR (DMSO-d$_6$) δ: 3.1 (3H, s), 5.5 (2H, s), 7.5 (1H, dt, J=8 Hz, 9.5 Hz), 8.0 (1H, ddd, J=2.5 Hz, 4.5 Hz, 9.5 Hz), 8.2 (1H, s).

REFERENCE EXAMPLE 22

Preparation of diethyl (6,7-difluoro-1H,4H-thiazolo[4,3-c][1,4]benzoxazin-1-ylidene)malonate [compound (XI) in which R$^4$ is ethyl]

Sodium hydride (3.3 g in oil, content: about 60 w/w %) was suspended in tetrahydrofuran (200 ml) and thereto diethyl malonate (13.2 g) was added dropwise at 20° C. and the mixture was stirred for 20 minutes. Then 6,7-difluoro-1-methylthio-4H-[1,4]benzoxazino[4,3-c]thiazolinium iodide (30 g) prepared in the same manner as in the previous Reference Example 21 was added at 10° C. and the mixture was stirred at room temperature for 1 hour. After the reaction mixture was evaporated to dryness under reduced pressure, cooled water was added and insoluble substance was filtered. The resultant was washed with water, dried and recrystallized from a mixed solvent of hexane-ethyl acetate to give the title compound (20 g) as pale yellow crystals. The compound had physical properties identical to those of diethyl (6,7-difluoro-1H,4H-thiazolo[4,3-c][1,4]benzoxazin-1-ylidene)malonate prepared in Reference Example 6.

REFERENCE EXAMPLE 23

Preparation of diethyl (6,7-difluoro-1H,4H-thiazolo[4,3-c][1,4]benzoxazin-1-ylidene)malonate [compound (XI) in which R$^4$ is ethyl]

6,7-Difluoro-1H,4H-thiazolo[4,3-c][1,4]benzoxazine-1-thione (0.4 g) prepared in Reference Example 18 and ethyl iodide (1.9 g) were added to acetonitrile (10 ml) and the mixture was stirred at 75° to 78° C. for 5 hours. Then diethyl malonate (0.5 g) and triethylamine (0.62 g) were added and the mixture was refluxed for 24 hours. After the reaction mixture was evaporated to dryness under reduced pressure, water was added to the residue and the mixture was extracted with chloroform. The extract was washed with a NaCl solution and dried over anhydrous sodium sulfate, followed by distilling off the solvent under reduced pressure. The residue was purified by silica-gel column chromatography (Silica gel 60, 230–400 meshes, made by Merck Co., 130 g, eluent; chloroform) under medium pressure and recrystallized from a mixed solvent of hexane-ethyl acetate to give the title compound (0.38 g) as pale yellow crystals. The compound had physical properties identical to those of diethyl (6,7-difluoro-1H,4H-thiazolo[4,3-c][1,4]benzoxazin-1-ylidene)malonate prepared in Reference Example 6.

REFERENCE EXAMPLE 24

Preparation of 9,1-epoxymethano-7,8-difluoro-5-oxo-5H-thiazolo[3,2-a]quinoline-4-carboxylic acid [compound (II) in which R is hydrogen atom]

A mixture of diethyl (6,7-difluoro-1H,4H-thiazolo[4,3-c][1,4]benzoxazin-1-ylidene)malonate (15 g) prepared in the same manner as in Reference Example 22 and polyphosphoric acid (125 g) was stirred with heating at 135° C. for 3 hours. Then concd. sulfuric acid (81 g) was added to the reaction mixture and the mixture was stirred at 135° C. for 2 hours. After a piece of ice was added to the reaction mixture, the resulting precipitate was filtered and washed with water, followed by recrystallization from dimethyl sulfoxide to give the title compound (9 g). The compound had physical properties identical to those of 9,1-epoxymethano-7,8-difluoro-5-oxo-5H-thiazolo[3,2-a]quinoline-4-carboxylic acid prepared in Reference Example 8.

REFERENCE EXAMPLE 25

Preparation of 9,1-epoxymethano-7-fluoro-8-(3-acetylamino-1-pyrrolidinyl)-5-oxo-5H-thiazolo[3,2-a]-quinoline-4-carboxylic acid [compound (IV) in which —NHCOR is acetylamino and —COOR is carboxyl]

7,8,9-Trifluoro-1-hydroxymethyl-5-oxo-5H-thiazolo[3,2-a]quinoline-4-carboxylic acid (2.5 g, see Reference Example 14), 3-acetylaminopyrrolidine (1.3 g, see the following Reference Example 27) and triethylamine (3.8 g) were added to dimethyl sulfoxide (180 ml) and the mixture was stirred at 78° to 82° C. for 3 hours and 20 minutes. The reaction solution was poured into ice-water and the mixture was adjusted to pH 6 with 3N hydrochloric acid. The precipitated crystals were filtered and washed with water and recrystallized from N,N-dimethylformamide to give the title compound (2.0 g) as yellow crystals, m.p. >300° C.

NMR (DMSO-d$_6$) δ: 1.8–1.9 (1H, m), 1.8 (3H, s), 2.0–2.2 (1H, m), 3.4–3.6 (1H, m), 3.7–3.8 (1H, m), 3.8–4.0 (2H, m), 4.2–4.4 (1H, m), 5.4–5.6 (2H, m), 7.5 (1H, d, J=14 Hz), 7.6 (1H, s), 8.2 (1H, d, J=6 Hz), 15.8 (1H, s).

IR (KBr) γ$_{max}$ cm$^{-1}$: 3372, 1668, 1622, 1470.

Elementary analysis for C$_{19}$H$_{16}$N$_3$O$_5$SF: Calcd. (%): C, 54.67; H, 3.86; N, 10.07. Found (%): C, 54.48; H, 4.07; N, 10.01.

REFERENCE EXAMPLE 26

Preparation of 1-hydroxypiperazine dihydrochloride [compound (XX) in which R$^1$ is hydrogen atom]

1-Hydroxypiperazine dihydrochloride was prepared by the following procedures (1) to (3).

(1) Preparation of 4-ethoxycarbonylethyl-1-formylpiperazine [compound (XXII) in which R$^1$ is hydrogen atom]

Ethyl acrylate (326 g) and chloroform (2 l) were added to 1-formylpiperazine (320 g) and the mixture was stirred at room temperature for 3 days. The solvent was distilled off under reduced pressure to give crude 4-ethoxycarbonylethyl-1-formylpiperazine (580 g).

NMR (CDCl$_3$) δ: 1.3 (3H, t, J=8 Hz), 2.3–2.9 (8H, m), 3.2–3.7 (4H, m), 4.0 (2H, q, J=8 Hz), 8.0 (1H, s).

(2) Preparation of 1-formyl-4-hydroxypiperazine [compound (XXIII) in which R$^1$ is hydrogen atom]

Water (500 ml) was added to the above crude 4-ethoxycarbonylethyl-1-formylpiperazine (114 g) to dissolve and thereto sodium tungstate dihydrate (7.25 g) was added. Thereto 31% aqueous hydrogen peroxide solution (82 ml) was added dropwise at 30° to 35° C. and the mixture was stirred at the same temperature for 1 hour. After further stirring the mixture at room temperature for 3 hours and then with heating at 50° to 55° C. for 5 hours, ethyl acetate (300 ml) was added and the mixture was shaken. The aqueous layer was separated and water was distilled off under reduced pressure to give black-brown oil, which was then purified by silica-gel column chromatography (silica gel 2 Kg, eluent: chloroform-methanol=10:1) and recrystallized from ethyl acetate to give 1-formyl-4-hydroxypiperazine (38.2 g), m.p. 118°–124° C.

Elementary analysis for C$_5$H$_{10}$N$_2$O$_2$: Calcd. (%): C, 46.14; H, 7.75; N, 21.52. Found (%): C, 46.12; H, 7.57; N, 21.55.

(3) Preparation of 1-hydroxypiperazine dihydrochloride:

3N Hydrochloric acid (50 ml) was added to 1-formyl-4-hydroxypiperazine (5.0 g) and the mixture was stirred at 77° to 87° C. for 20 minutes. After stirring, water was distilled off under reduced pressure to give a pale yellow residue, which was washed with ethanol and recrystallized from a mixed solvent of water-ethanol to give 1-hydroxypiperazine dihydrochloride (5.0 g) as light brown prisms, m.p. 164°–175° C. (dec.).

Mass spectrum (m/e): 102 (M+), 85 (M+—OH).

IR (KBr) γ$_{max}$ cm$^{-1}$: 3240, 3010, 2720, 1558, 1501, 1452, 1448, 1433.

NMR (DMSO-d$_6$) δ: 3.1–3.8 (m), 9.4–10.1 (m).

Elementary analysis for C$_4$H$_{10}$N$_2$O·2HCl: Calcd. (%): C, 27.44; H, 6.91; N, 16.00. Found (%): C, 27.18; H, 6.96; N, 15.97.

REFERENCE EXAMPLE 27

Preparation of 3-acetylaminopyrrolidine

3-Acetylaminopyrrolidine was prepared by the following two-step procedure.

(1) Preparation of 3-acetylamino-1-benzylpyrrolidine:

3-Amino-1-benzylpyrrolidine [8.3 g, prepared by a method of G. C. Helsley et al., J. Med. Chem. 11, 1034 (1968)] was dissolved in methylene chloride (40 ml) and thereto acetic anhydride (5.3 g) was added dropwise with stirring under cooling with ice-water and the mixture was stirred for 1.5 hours. After addition of 2N sodium hydroxide (40 ml), the mixture was extracted with methylene chloride. The extract was washed with water and dried over anhydrous magnesium sulfate, followed by distilling off the solvent under reduced pressure to give 3-acetylamino-1-benzylpyrrolidine (9.0 g) as oil.

NMR (CDCl$_3$) δ: 1.3–3.1 (6H, m), 1.9 (3H, s), 3.6 (2H, s), 4.1–4.7 (1H, m), 5.8–6.5 (1H, bd), 7.0–7.5 (5H, m).

(2) Preparation of 3-acetylaminopyrrolidine:

To a solution of the above 3-acetylamino-1-benzylpyrrolidine (4.0 g) in ethanol (30 ml) was added 10% palladium-carbon (0.8 g) in water (1 ml). The mixture was shaken at room temperature for 22 hours under hydrogen pressure of 55 p.s.i. using Parr hydrogenator. The catalyst was filtered off and the solvent was distilled off under reduced pressure. The residue was dissolved in chloroform and dried over anhydrous magnesium sulfate, followed by distilling off the solvent to give 3-acetylaminopyrrolidine (2.3 g) as oil.

NMR (CDCl$_3$) δ: 1.3–2.5 (2H, m), 1.9 (3H, s), 2.5–3.3 (4H, m), 2.7 (1H, s), 4.0–4.6 (1H, m), 6.9–7.5 (1H, bd).

EXAMPLE 1

Preparation of 9,1-epoxymethano-7-fluoro-8-(4-methyl-1-piperazinyl)-5-oxo-5H-thiazolo[3,2-a]quinoline-4-carboxylic acid [compound (I) in which Z is 4-methyl-1-piperazinyl] and hydrochloride thereof by the process (A)

(a) Preparation of 9,1-epoxymethano-7-fluoro-8-(4-methyl-1-piperazinyl)-5-oxo-5H-thiazolo[3,2-a]quinoline-4-carboxylic acid:

9,1-Epoxymethano-7,8-difluoro-5-oxo-5H-thiazolo-[3,2-a]quinoline-4-carboxylic acid (0.13 g, prepared in accordance with Reference Example 8) and 1-methylpiperazine (0.25 g) were added to dimethyl sulfoxide (6 ml) and the mixture was stirred at 85° C. for 2.5 hours. The reaction mixture was concentrated to dryness under reduced pressure and thereto water (30 ml) and acetic acid (6 ml) were added, followed by filtering off insoluble substance. The filtrate was adjusted to pH 7 by adding a saturated sodium hydrogen carbonate solution and the resultant was extracted with a mixed solvent of chloroform-methanol (10:1). After the extract was washed with water and the solvent was distilled off under reduced pressure, the residue was recrystallized from a mixed solvent of chloroform-ethanol to give the title compound (0.12 g) as pale yellow crystals, m.p. 255° C. (dec.).

NMR (DMSO-d$_6$, D$_2$O treatement) δ: 2.3 (3H, s), 2.4–2.5 (4H, m), 3.3–3.4 (4H, m), 5.5 (2H, s), 7.5 (1H, d, J=12 Hz), 7.6 (1H, s).

IR (KBr) γ$_{max}$cm$^{-1}$: 2842, 2800, 1688, 1620, 1472, 1448, 1396.

Elementary analysis for $C_{18}H_{16}N_3O_4SF$: Calcd. (%): C, 55.52; H, 4.14; N, 10.79. Found (%): C, 55.52; H, 4.15; N, 10.50.

(b) Preparation of hydrochloride of the compound (a):

9,1-Epoxymethano-7-fluoro-8-(4-methyl-1-piperazinyl)-5-oxo-5H-thiazolo[3,2-a]quinoline-4-carboxylic acid (0.60 g) was dissolved in dilute hydrochloric acid (40 ml) and the mixture was filtered. The filtrate was cooled with ice-water to precipitate crystals, which were filtered and washed with 1N hydrochloric acid and then with ethanol to give 9,1-epoxymethano-7-fluoro-8-(4-methyl-1-piperazinyl)-5-oxo-5H-thiazolo[3,2-a]quinoline-4-carboxylic acid hydrochloride (0.39 g) as pale yellow crystals, m.p. 287° C. (dec.).

NMR ($D_2O$) δ: 3.0 (3H, s), 3.3–3.4 (2H, m), 3.5–3.8 (6H, m), 5.4 (2H, s), 6.8 (1H, d, J=12 Hz), 7.4 (1H, s)

IR (KBr) $\gamma_{max}cm^{-1}$: 1690, 1620, 1479.

Elementary analysis for $C_{18}H_{16}N_3O_4SF \cdot HCl$: Calcd. (%): C, 50.77; H, 4.02; N, 9.87. Found (%): C, 50.63; H, 4.09; N, 9.72.

EXAMPLE 2

Preparation of 9,1-epoxymethano-7-fluoro-8-(1-piperazinyl)-5-oxo-5H-thiazolo[3,2-a]quinoline-4-carboxylic acid [compound (I) in which Z is 1-piperazinyl] and hydrochloride thereof by the process (B)

(a) Preparation of 9,1-epoxymethano-7-fluoro-8-(1-piperazinyl)-5-oxo-5H-thiazolo[3,2-a]quinoline-4-carboxylic acid:

7,8,9-Trifluoro-1-hydroxymethyl-5-oxo-5H-thiazolo[3,2-a]quinoline-4-carboxylic acid (0.5 g) prepared in the same manner as in Reference Example 14 and piperazine (0.8 g) were added to dimethyl sulfoxide (20 ml) and the mixture was stirred at 73° C. for 35 minutes. The reaction mixture was concentrated to dryness under reduced pressure. To the concentrate were added water (50 ml) and actetic acid (6 ml) and insoluble substance was filtered off. The filtrate was adjusted to pH 7 by adding a saturated aqueous sodium hydrogen carbonate solution. The precipitated crystals were filtered, washed with water and recrystallized from N,N-dimethylformamide to give the title compound (0.41 g) as pale yellow crystals, m.p. 255° C.(dec.).

NMR (DMSO-$d_6$) δ: f2.8–2.9 (4H, m), 3.2–3.3 (4H, m), 5.6 (2H, s), 7.6 (1H, d, J=12 Hz), 7.6 (1H, s.

IR (KBr) $\gamma_{max}cm^{-1}$: 3196, 2836, 1696, 1618, 1472, 1397.

Elementary analysis for $C_{17}H_{14}N_3O_4SF$: Calcd. (%): C, 54.39; H, 3.76; N, 11.19. Found (%): C, 54.28; H, 3.86; N, 10.99.

(b) Preparation of hydrochloride of compound (a):

To 9,1-epoxymethano-7-fluoro-8-(1-piperazinyl)-5-oxo-5H:thiazolo[3,2-a]quinoline-4-carboxylic acid (0.58 g) was added dilute hydrochloric acid (50 ml) and the mixture was warmed at 40° C. to dissolve. The solution was filtered and the filtrate was cooled with ice-water to precipitate crystals, which were filtered and washed with 1N hydrochloric acid and then with ethanol to give 9,1-epoxymethano-7-fluoro-8-(1-piperazinyl)-5-oxo-5H-thiazolo[3,2-a]quinoline-4-carboxylic acid hydrochloride (0.46 g), m.p. >300° C.

NMR ($D_2O$) δ: 3.4–3.5 (4H, m), 3.6–3.7 (4H, m), 5.3 (2H, s), 6.8 (1H, d, J=12 Hz), 7.4 (1H, s).

IR (KBr) $\gamma_{max}cm^{-1}$: 1683, 1619, 1477.

Elementary analysis for $C_{17}H_{14}N_3O_4SF \cdot HCl \cdot \frac{1}{2}H_2O$: Calcd. (%): C, 48.52; H, 3.83; N, 9.98. Found (%): C, 48.69; H, 3.75; N, 10.04.

EXAMPLE 3

Preparation of 9,1-epoxymethano-7-fluoro-8-(3-methyl-1-piperazinyl)-5-oxo-5H-thiazolo[3,2-a]quinoline-4-carboxylic acid [compound (I) in which Z is 3-methyl-1-piperazinyl] by the process (A)

9,1-Epoxymethano-7,8-difluoro-5-oxo-5H-thiazolo[3,2-a]quinoline-4-carboxylic acid (0.5 g) prepared in the same manner as in Reference Example 8 and 2-methylpiperazine (0.81 g) were added to dimethyl sulfoxide (10 ml) and the mixture was stirred at 80° to 85° C. for 35 minutes. The reaction mixture was concentrated to dryness under reduced pressure. To the concentrate was added dilute hydrochloric acid (50 ml) and insoluble substance was filtered off. The filtrate was adjusted to pH 7 by adding 10% aqueous sodium hydroxide solution to precipitate crystals, which were filtered, washed with water and recrystallized from a mixed solvent of ethanol-N,N-dimethylformamide to give the title compound (0.33 g) as pale yellow crystals, m.p. 240° C. (dec.).

NMR (DMSO-$d_6$, $D_2O$ treatment) δ: 1.0 (3H, d, J=4 Hz), 2.7–3.4 (7H, m), 5.5 (2H, s), 7.5 (1H, d, J=12 Hz), 7.6 (1H, s).

IR (KBr) $\gamma_{max}cm^{-1}$: 3250, 2840, 1700, 1621, 1470.

Elementary analysis for $C_{18}H_{16}N_3O_4SF \cdot \frac{1}{4}H_2O$: Calcd. (%): C, 54.88; H, 4.22; N, 10.67. Found (%): C, 54.77; H, 4.17; N, 10.46.

EXAMPLE 4

Preparation of 9,1-epoxymethano-7-fluoro-8-(4-hydroxy-1-piperazinyl)-5-oxo-5H-thiazolo[3,2-a]quinoline-4-carboxylic acid [compound (I) in which Z is 4-hydroxy-1-piperazinyl] by the process (B)

7,8,9-Trifluoro-1-hydroxymethyl-5-oxo-5H-thiazolo[3,2-a]quinoline-4-carboxylic acid (0.5 g) prepared in the same manner as in Reference Example 14, 1-hydroxypiperazine dihydrochloride (0.41 g) prepared in the same manner as in Reference Example 26 and triethylamine (1.23 g) were added to dimethyl sulfoxide (20 ml) and the mixture was stirred at 75° to 85° C. for 45 hours. The reaction mixture was concentrated to dryness under reduced pressure. To the concentrate was added dilute hydrochloric acid (500 ml) and the mixture was warmed at 50° C. to dissolve, followed by filtering off insoluble substance. The filtrate was adjusted to pH 7 by adding a saturated aqueous sodium carbonate solution to precipitate crystals, which were filtered, washed with water and recrystallized from dimethyl sulfoxide containing water to give the title compound (0.24 g) as pale yellow crystals, m.p. 248° C. (dec.).

NMR (DMSO-$d_6$) δ: 2.6–2.7 (2H, m), 3.1–3.2 (2H, m), 3.3–3.4 (2H, m), 3.4–3.5 (2H, m), 5.6 (2H, s), 7.6 (1H, d, J=12 Hz), 7.6 (1H, s), 8.2 (1H, s), 15.5 (1H, bs).

IR (KBr) $\gamma_{max}cm^{-1}$: 2852, 1681, 1619, 1482.

Elementary analysis for $C_{17}H_{14}N_3O_5SF \cdot \frac{1}{4}H_2O$: Calcd. (%): C, 51.58; H, 3.69; N, 10.61. Found (%): C, 51.66; H, 3.57; N, 10.56.

EXAMPLE 5

Preparation of
9,1-epoxymethano-7-fluoro-8-(1-pyrrolidinyl)-5-oxo-5H-thiazolo[3,2-a]quinoline-4-carboxylic acid
[compound (I) in which Z is 1-pyrrolidinyl] by the process (B)

7,8,9-Trifluoro-1-hydroxymethyl-5-oxo-5H-thiazolo[3,2-a]quinoline-4-carboxylic acid (0.5 g) prepared in the same manner as in Reference Example 14 and pyrrolidine (0.7 g) were added to dimethyl sulfoxide (20 ml) and the mixture was stirred at 75° C. for 2 hours and 15 minutes. The precipitated crystals were filtered, washed with water and recrystallized from dimethyl sulfoxide to give the title compound (0.3 g) as yellow crystals, m.p. >300° C.

NMR (DMSO-$d_6$) δ: 1.8–2.0 (4H, m), 3.6–3.8 (4H, m), 5.5 (2H, s), 7.5 (1H, d, J=14 Hz), 7.6 (1H, s), 15.8 (1H, s).

IR (KBr) $\gamma_{max}$cm$^{-1}$: 2880, 1693, 1619, 1601, 1477, 1465, 1390.

Elementary analysis for $C_{17}H_{13}N_2O_4SF$: Calcd. (%): C, 56.66; H, 3.64; N, 7.77. Found (%): C, 56.59; H, 3.65; N, 7.57.

EXAMPLE 6

Preparation of
9,1-epoxymethano-7-fluoro-8(3-hydroxy-1-pyrrolidinyl)-5-oxo-5H-thiazolo[3,2-a]quinoline-4-carboxylic acid [compound (I) in which Z is 3-hydroxy-1-pyrrolidinyl] by the process (B)

7,8,9-Trifluoro-1-hydroxymethyl-5-oxo-5H-thiazolo[3,2-a]quinoline-4-carboxylic acid (0.5 g) prepared in the same manner as in Reference Example 14, 3-hydroxypyrrolidine (0.16 g) and triethylamine (0.93 g) were added to dimethyl sulfoxide (20 ml) and the mixture was stirred at 75° C. for 1 hour and 45 minutes. The precipitated crystals were filtered, washed with water and recrystallized from dimethyl sulfoxide to give the title compound (0.35 g) as yellow crystals, m.p. >300° C.

NMR (DMSO-$d_6$) δ: 1.8–2.0 (2H, m), 3.4–3.5 (1H, m), 3.6–3.7 (1H, m), 3.9–4.1 (2H, m), 4.3–4.4 (1H, m), 5.0 (1H, d, J=3 Hz), 5.4 (1H, d, J=14 Hz), 5.5 (1H, d, J=14 Hz), 7.5 (1H, d, J=14 Hz), 7.6 (1H, s), 15.8 (1H, s).

IR (KBr) $\gamma_{max}$cm$^{-1}$: 1670, 1618, 1471, 1391.

Elementary analysis for $C_{17}H_{13}N_2O_5SF$: Calcd. (%): C, 54.25; H, 3.48; N, 7.44. Found (%): C, 54.26; H, 3.54; N, 7.26.

EXAMPLE 7

Preparation of
9,1-epoxymethano-7-fluoro-8-(3-amino-1-pyrrolidinyl)-5-oxo-5H-thiazolo[3,2-a]quinoline-4-carboxylic acid [compound (I) in which Z is 3-amino-1-pyrrolidinyl] by the process (C)

To 9,1-epoxymethano-7-fluoro-8-(3-acetylamino-1-pyrrolidinyl)-5-oxo-5H-thiazolo[3,2-a]quinoline-4-carboxylic acid (1.5 g) prepared in the same manner as in Reference Example 25 was added 10% aqueous sodium hydroxide (400 ml) and the mixture was refluxed with stirring for 15 hours. The reaction mixture was adjusted to pH 7 with 3N hydrochloric acid to precipitate crystals, which were filtered, washed with water and recrystallized from N,N-dimethylformamide to give the title compound (0.82 g) as green-yellow crystals, m.p. >300° C.

NMR (DMSO-$d_6$) δ: 1.6–1.8 (1H, m), 1.9–2.1 (1H, m), 2.9–4.1 (m), 5.4 (2H, s), 7.5 (1H, d, J=14 Hz), 7.6 (1H, s).

IR (KBr) $\gamma_{max}$cm$^{-1}$: 1600, 1558, 1464, 1390, 1368.

EXAMPLE 8

Preparation of
9,1-epoxymethano-7-fluoro-8-(4-methyl-1-piperazinyl)-5-oxo-5H-thiazolo[3,2-a]quinoline-4-carboxylic acid [compound (I) in which Z is 4-methyl-1-piperazinyl] by the process (B)

7,8,9-Trifluoro-1-hydroxymethyl-5-oxo-5H-thiazolo]3,2-a]quinoline-4-carboxylic acid (2.7 g) prepared in the same manner as in Reference Example 14 and 1-methyl-piperazine (3.3 g) were added to dimethyl sulfoxide (50 ml) and the mixture was stirred at 80° C. for 4 hours. The reaction mixture was concentrated to dryness under reduced pressure. To the concentrate were added water (130 ml) and acetic acid (6 ml) and insoluble substance was filtered off. The filtrate was adjusted to pH 7 by adding 10% aqueous sodium hydroxide and the resultant was extracted with a mixed solvent of chloroform-methanol (10:1). The extract was washed with water and the solvent was distilled off under reduced pressure. The residue was recrystallized from a mixed solvent of chloroform-ethanol to give the title compound (2.1 g) as pale yellow crystals. The compound thus obtained had physical properties identical to those of 9,1-epoxymethano-7-fluoro-8-(4-1-piperazinyl)-5-oxo-5H-thiazolo[3,2-a]quinoline-4-carboxylic acid prepared in Example 1-(a).

EXAMPLE 9

Preparation of
9,1-epoxymethano-7-fluoro-8-(4-methyl-1-piperazinyl)-5-oxo-5H-thiazolo[3,2-a]quinoline-4-carboxylic acid [compound (I) in which Z is 4-methyl-1-piperazinyl] by the process (A)

(1) Preparation of ethyl 9,1-epoxymethano-7-fluoro-8-(4-methyl-1-piperazinyl)-5-oxo-5H-thiazolo[3,2-a]quinoline-4-carboxylate:

Ethyl 9,1-epoxymethano-7,8-difluoro-5-oxo-5H-thiazolo[3,2-a]quinoline-4-carboxylate (0.34 g) prepared in the same manner as in Reference Example 7 and 1-methyl-piperazine (0.31 g) were added to dimethyl sulfoxide (30 ml) and the mixture was stirred at 105° C. for 52 hours. To the reaction mixture was added ice-water and insoluble substance was filtered, washed with water and recrystallized from a mixed solvent of chloroform-ethanol to give the title compound (0.29 g) as pale yellow crystals, m.p. 265° C. (dec.).

NMR (CDCl$_3$) δ: 1.5 (3H, t, J=7 Hz), 2.4 (3H, s), 2.5–2.6 (4H, m), 3.3–3.4 (4H, m), 4.5 (2H, q, J=7 Hz), 5.3 (2H, d, J=1 Hz), 6.8 (1H, t, J=1 Hz), 7.7 (1H, d, J=12 Hz).

IR (KBr) $\gamma_{max}$cm$^{-1}$: 3066, 1652, 1605, 1570, 1478, 1462.

Elementary analysis for $C_{20}H_{20}N_3O_4SF$: Calcd. (%): C, 57.54; H, 4.83; N, 10.07. Found (%): C, 57.47; H, 4.70; N, 9.81.

(2) Preparation of 9,1-epoxymethano-7-fluoro-8-(4-methyl-1-piperazinyl)-5-oxo-5H-thiazolo[3,2-a]quinoline-4-carboxylic acid:

The above prepared ethyl 9,1-epoxymethano-7-fluoro-8-(4-methyl-1-piperazinyl)-5-oxo-5H- thiazolo[3,2-a]quinoline-4-carboxylate (0.24 g) and 1N sodium hydroxide (1.2 ml) were added to ethanol (100 ml) and the mixture was refluxed for 2 hours. The reaction mixture was concentrated to dryness under reduced pressure. To the concentrate were added water (50 ml) and acetic acid (0.5 ml) and insoluble substance was filtered off. The filtrate was adjusted to pH 7 by adding 1N sodium hydroxide and the resultant was extracted with a mixed solvent of chloroform-methanol (10:1). The extract was concentrated to dryness under reduced pressure. The residue was washed with water and recrystallized from a mixed solvent of chloroform-ethanol to give the title compound (0.11 g) as pale yellow crystal. The compound thus obtained had physical properties identical to those of 9,1-epoxymethano-7-fluoro-8-(4-methyl-1-piperazinyl)-5-oxo-5H-thiazolo[3,2-a]quinoline-4-carboxylic acid prepared in Reference Example 1-(a).

EXAMPLE 10

Employing 1-ethylpiperazine in place of 1-methylpiperazine, the procedure of Example 1 was repeated to give the following compounds.

(a) 9,1-Epoxymethano-7-fluoro-8-(4-ethyl-1-piperazinyl)-5-oxo-5H-thiazolo[3,2-a]quinoline-4-carboxylic acid [compound (I) in which Z is 4-ethyl-1-piperazinyl]:

Color: pale yellow.
Melting point: 249° C. (dec.).
NMR (DMSO-$d_6$, $D_2O$ treatment) δ: 1.1 (3H, t, J=7 Hz), 2.4 (2H, q, J=7 Hz), 2.4–2.5 (4H, m), 3.3–3.4 (4H, m), 5.5 (2H, s), 7.5 (1H, d, J=12 Hz), 7.6 (1H, s).
IR (KBr) $\gamma_{max}$cm$^{-1}$: 1703, 1620, 1479.
Elementary analysis for $C_{19}H_{18}N_3O_4SF\cdot\frac{1}{2}H_2O$: Calcd. (%): C, 55.33; H, 4.64; N, 10.19. Found (%): C, 55.42; H, 4.56; N, 10.08.

(b) 9,1-Epoxymethano-7-fluoro-8-(4-ethyl-1-piperazinyl)-5-oxo-5H-thiazolo[3,2-a]quinoline-4-carboxylic acid hydrochloride [hydrochloride of compound (I) in which Z is 4-ethyl-1-piperazinyl]:

Color: pale yellow.
Melting point: 289° C. (dec.).
NMR ($D_2O$) δ: 1.4 (3H, d, J=7 Hz), 3.4 (2H, d, J=7 Hz), 3.2–3.5 (2H, m), 3.5–3.8 (6H, m), 5.4 (2H, s), 6.9 (1H, d, J=12 Hz), 7.4 (1H, s).
IR (KBr) $\gamma_{max}$cm$^{-1}$: 1692, 1622, 1475.
Elementary analysis for $C_{19}H_{18}N_3O_4SF\cdot HCl\cdot\frac{1}{2}H_2O$: Calcd. (%): C, 50.84; H, 4.49; N, 9.36. Found (%): C, 50.99; H, 4.42; N, 9.32.

EXAMPLE 11

Preparation of Tablets

Tablets each containing 100 mg of 9,1-epoxymethano-7-fluoro-8-(4-methyl-1-piperazinyl)-5-oxo-5H-thiazolo[3,2-a]quinoline-4-carboxylic acid [compound prepared in Example 1-(a)] were prepared as follows:

| (Formula) | |
|---|---|
| Ingredients | Part by weight |
| The active ingredient (Compound prepared in Example 1-(a) | 100 |
| Corn starch | 46 |
| Microcrystalline cellulose | 98 |
| Hydroxypropyl cellulose | 2 |
| Magnesium stearate | 4 |

Procedure

To a mixture of the active ingredient, corn starch and microcrystalline cellulose were added a solution of hydroxypropyl cellulose in water (50 parts by weight) and the mixture was kneaded well. The kneaded mixture was passed through a mesh to produce granules. After drying the granules, magnesium stearate was mixed with the granules and the mixture was tabletted by a conventional method to give tablets (each 250 mg).

EXAMPLE 12

Preparation of Granules

Granules each containing 9,1-epoxymethano-7-fluoro-8-(4-methyl-1-piperazinyl)-5-oxo-5H-thiazolo[3,2-a]quinoline-4-carboxylic acid hydrochloride [compound prepared in Example 1-(b)] (200 mg) per 500 mg granules were prepared as follows:

| (Formula) | |
|---|---|
| Ingredients | Part by weight |
| The active ingredient (compound prepared in Example 1-(b) | 200 |
| Lactose | 185 |
| Corn starch | 109 |
| Hydroxypropyl cellulose | 6 |

Procedure

To a mixture of the active ingredient, lactose and corn starch was added a solution of hydroxypropyl cellulose in water (120 part by weight) and the mixture was kneaded well. The kneaded mixture was passed through a No. 20 mesh sieve to produce granules. The granules were dried and passed through a sieve of desired size to yield the granules.

EXAMPLE 13

Preparation of Capsules

Capsules each containing 100 mg of 9,1-epoxymethano-7-fluoro-8-(4-methyl-1-piperazinyl)-5-oxo-5H-thiazolo]3,2-a]quinoline-4-carboxylic acid hydrochloride [compound prepared in Example 1-(b)] were prepared as follows:

| (Formula) | |
|---|---|
| Ingredients | Part by weight |
| The active ingredient [compound prepared in Example 1-(b)] | 100 |
| Lactose | 35 |
| Corn starch | 60 |
| Magnesium stearate | 5 |

Procedure

All the above ingredients were mixed thoroughly and the resulting powdery mixture was packed into gelatin capsules in each amount of 200 mg.

EXAMPLES 14–16

Preparation of Tablets

Tablets each containing 100 mg of 9,1-epoxymethano-7-fluoro-8-(4-methyl-1-piperazinyl)-5-oxo-5H-thiazolo[3,2-a]quinoline-4-carboxylic acid hydrochloride [compound prepared in Example 1-(b)], 9,1-epoxymethano-7-fluoro-8-(1-piperazinyl)-5-oxo-5H- thiazolo[3,2-a]quinoline-4-carboxylic acid hydrochloride [compound prepared in Example 2-(b)], or 9,1-epoxymethano-7-fluoro-8-(3-methyl-1-piperazinyl)-5-oxo-5H-thiazolo[3,2-a]quinoline-4-carboxylic acid (compound prepared in Example 3) were prepared by the procedure as described in Example 11 except that the compound of Example 1-(b), 2-(b) or 3 was employed in place of the compound prepared in Example 1-(a) as the active ingredient.

EXAMPLES 17–19

Preparation of Granules

Granules each containing 9,1-epoxymethano-7-fluoro-8-(4-methyl-1-piperazinyl)-5-oxo-5H-thiazolo[3,2-a]quinoline-4-carboxylic acid [compound prepared in Example 1-(a)], 9,1-epoxymethano-7-fluoro-8-(1-piperazinyl)-5-oxo-5H-thiazolo[3,2-a]quinoline-4-carboxylic acid hydrochloride [compound prepared in Example 2-(b)], or 9,1-epoxymethano-7-fluoro-8-(4-hydroxy-1-piperazinyl)-5-oxo-5H-thiazolo[3,2-a]quinoline-4-carboxylic acid (compound prepared in Example 4) were prepared by the procedure as described in Example 12 except that the compound of Examples 1-(a), 2-(b) or 4 was employed in place of the compound prepared in Example 1-(b) as the active ingredient.

EXAMPLES 20–21

Preparation of Capsules

Capsules each containing 100 mg of 9,1-epoxymethano-7-fluoro-8-(4-methyl-1-piperazinyl)-5-oxo-5H-thiazolo[3,2-a]quinoline-4-carboxylic acid [compound prepared in Example 1-(a)], or 9,1-epoxymethano-7-fluoro-8-(3-hydroxy-1-pyrrolidinyl)-5-oxo-5H-thiazolo[3,2-a]quinoline-4-carboxylic acid (compound prepared in Example 6) were prepared in the procedure as described in Example 13 except that the compound of Example 1-(a) or 6 was employed in place of the compound prepared in Example 1-(b) as the active ingredient.

What is claimed is:

1. A compound of the formula (II):

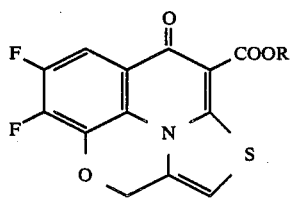

(II)

wherein R is hydrogen atom or a lower alkyl.

2. A compound of the formula (III):

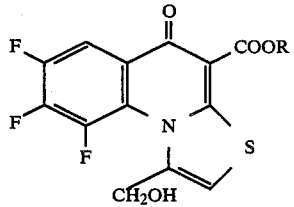

(III)

wherein R is hydrogen atom or a lower alkyl.

* * * * *